(12) United States Patent
Li

(10) Patent No.: US 11,547,746 B2
(45) Date of Patent: Jan. 10, 2023

(54) METHOD FOR TREATING CORONARY ATHEROSCLEROSIS AND COMPLICATIONS THEREOF

(71) Applicant: Talengen International Limited, Wanchai (HK)

(72) Inventor: Jinan Li, Guangdong (CN)

(73) Assignee: Talengen International Limited, Hong Kong (CN)

(*) Notice: Subject to any disclaimer, the term of this patent is extended or adjusted under 35 U.S.C. 154(b) by 540 days.

(21) Appl. No.: 16/469,599

(22) PCT Filed: Jun. 19, 2017

(86) PCT No.: PCT/CN2017/089044
§ 371 (c)(1),
(2) Date: Jun. 13, 2019

(87) PCT Pub. No.: WO2018/107685
PCT Pub. Date: Jun. 21, 2018

(65) Prior Publication Data
US 2020/0078449 A1 Mar. 12, 2020

(30) Foreign Application Priority Data

Dec. 15, 2016 (WO) ............... PCT/CN2016/110168
Dec. 15, 2016 (WO) ............... PCT/CN2016/110172

(51) Int. Cl.
*A61K 38/48* (2006.01)
*A61P 9/10* (2006.01)
*A61P 3/06* (2006.01)
*A61P 3/10* (2006.01)
*A61P 1/16* (2006.01)
*A61P 9/00* (2006.01)
*A61K 45/06* (2006.01)

(52) U.S. Cl.
CPC ............ *A61K 38/484* (2013.01); *A61P 1/16* (2018.01); *A61P 3/06* (2018.01); *A61P 3/10* (2018.01); *A61P 9/00* (2018.01); *A61P 9/10* (2018.01); *A61K 45/06* (2013.01); *C12Y 304/21007* (2013.01)

(58) Field of Classification Search
None
See application file for complete search history.

(56) References Cited

U.S. PATENT DOCUMENTS

| 4,245,051 A | 1/1981 | Reich |
| 4,996,050 A | 2/1991 | Tsukada |
| 5,304,383 A * | 4/1994 | Eibl ............... C12Y 304/21007 424/499 |
| 5,597,800 A | 1/1997 | Eibl et al. |
| 5,776,452 A | 7/1998 | Eibl |
| 7,067,492 B2 | 6/2006 | Ny et al. |
| 8,318,661 B2 | 11/2012 | Ny et al. |
| 8,357,147 B2 | 1/2013 | Burkinshaw et al. |
| 8,637,010 B2 | 1/2014 | Ny et al. |
| 8,679,482 B2 | 3/2014 | Ny et al. |
| 10,086,052 B2 | 10/2018 | Ny et al. |
| 10,864,257 B2 | 12/2020 | Li |
| 2002/0103129 A1 | 8/2002 | Ge |
| 2002/0159992 A1 | 10/2002 | Henkin |
| 2003/0026798 A1 | 2/2003 | Zimmerman |
| 2003/0054988 A1 | 3/2003 | Ji |
| 2003/0147876 A1 | 8/2003 | Ni |
| 2005/0124036 A1 | 6/2005 | Susilo |
| 2008/0176934 A1 | 7/2008 | Verbeuren |
| 2008/0200387 A1 | 8/2008 | Wu et al. |
| 2009/0208448 A1 | 8/2009 | Solomon |
| 2009/0275513 A1 | 11/2009 | Rebbeor |
| 2010/0028321 A1 | 2/2010 | Ny et al. |
| 2010/0099600 A1 | 4/2010 | Ny |
| 2010/0184661 A1 | 7/2010 | Luo |
| 2012/0022080 A1 | 1/2012 | Miyata |
| 2012/0114630 A1 | 5/2012 | Zwaal |
| 2014/0273275 A1 | 9/2014 | Jacobs |
| 2016/0184411 A1 | 6/2016 | Ny et al. |

(Continued)

FOREIGN PATENT DOCUMENTS

| CA | 2145841 A1 | 10/1995 |
| CA | 2707266 A1 | 12/2013 |

(Continued)

OTHER PUBLICATIONS

Beckman et al. "Diabetes and atherosclerosis: epidemiology, pathophysiology, and management" JAMA May 15, 2002;287(19):2570-81. (Year: 2002).*

(Continued)

*Primary Examiner* — Thane Underdahl
(74) *Attorney, Agent, or Firm* — Morrison & Foerster LLP

(57) ABSTRACT

The present invention relates to a method for preventing and/or treating coronary atherosclerosis and its related conditions in a subject, comprising administering a prophylactically and/or therapeutically effective amount of plasminogen to the subject, wherein the subject suffers from, is suspected of suffering from coronary atherosclerosis and its related conditions, or has a risk of suffering from coronary atherosclerosis and its related conditions. The present invention further relates to a medicament, a pharmaceutical composition, an article of manufacture, and a kit comprising plasminogen which are useful for preventing and/or treating coronary atherosclerosis and its related conditions in a subject.

19 Claims, 8 Drawing Sheets
Specification includes a Sequence Listing.

(56) References Cited

U.S. PATENT DOCUMENTS

| | | |
|---|---|---|
| 2019/0083586 A1 | 3/2019 | Li |
| 2019/0231854 A1 | 8/2019 | Robitaille |
| 2019/0343931 A1 | 11/2019 | Li |

FOREIGN PATENT DOCUMENTS

| | | |
|---|---|---|
| CA | 3002915 A1 | 5/2017 |
| CN | 1451746 A | 10/2003 |
| CN | 1662548 A | 8/2005 |
| CN | 1768138 A | 5/2006 |
| CN | 101015686 A | 8/2007 |
| CN | 101132788 A | 2/2008 |
| CN | 101573134 A | 11/2009 |
| CN | 101628113 A | 1/2010 |
| CN | 101918548 A | 12/2010 |
| CN | 102121023 A | 7/2011 |
| CN | 102123721 A | 7/2011 |
| CN | 102199587 A | 9/2011 |
| CN | 102378753 A | 3/2012 |
| CN | 102482338 A | 5/2012 |
| CN | 103384722 A | 11/2013 |
| CN | 103656630 A | 3/2014 |
| CN | 103764163 A | 4/2014 |
| CN | 104274449 A | 1/2015 |
| CN | 105008323 A | 10/2015 |
| EP | 0307847 B1 | 12/1992 |
| EP | 0631786 A1 | 1/1995 |
| EP | 0674906 A2 | 10/1995 |
| EP | 3391902 A1 | 10/2018 |
| EP | 3556391 A1 | 10/2019 |
| JP | S62153224 A | 7/1987 |
| JP | 7145076 A | 6/1995 |
| JP | 2005507244 A | 3/2005 |
| JP | 2005525798 A | 9/2005 |
| JP | 2008534508 A | 8/2008 |
| JP | 2010502600 A | 1/2010 |
| JP | 2010515694 A | 5/2010 |
| JP | 2012532596 A | 12/2012 |
| JP | 6783870 B | 1/2019 |
| JP | 2019500423 A | 1/2019 |
| JP | 2019500424 A | 1/2019 |
| JP | 2020502154 A | 1/2020 |
| JP | 2020502156 A | 1/2020 |
| JP | 2020511416 A | 4/2020 |
| TW | 201441186 A | 11/2014 |
| TW | 201625294 A | 7/2016 |
| TW | I624268 B | 5/2018 |
| TW | 201822791 A | 7/2018 |
| TW | 201822792 A | 7/2018 |
| TW | 201822799 | 7/2018 |
| TW | 201822805 A | 7/2018 |
| TW | 201822806 A | 7/2018 |
| TW | 201822809 A | 7/2018 |
| TW | 201822810 A | 7/2018 |
| TW | 201829448 A | 8/2018 |
| TW | 200908973 A | 3/2019 |
| WO | WO-9401128 A1 * | 1/1994 ........... A61K 38/166 |
| WO | 199512407 A1 | 5/1995 |
| WO | 199900420 A1 | 1/1999 |
| WO | WO200048595 A1 | 8/2000 |
| WO | WO200049871 A1 | 8/2000 |
| WO | 200240510 A2 | 5/2002 |
| WO | 2003014145 A2 | 2/2003 |
| WO | 2003033019 A2 | 4/2003 |
| WO | 200240510 A3 | 6/2003 |
| WO | 2003033019 A3 | 7/2003 |
| WO | 2003066842 A2 | 8/2003 |
| WO | 2003090512 A2 | 11/2003 |
| WO | 2003090512 A3 | 11/2003 |
| WO | 2003014145 A3 | 12/2003 |
| WO | 2003066842 A3 | 6/2004 |
| WO | 2006102395 A2 | 9/2006 |
| WO | 2006122249 A2 | 11/2006 |
| WO | 2006102395 A3 | 5/2007 |
| WO | 2006122249 A3 | 6/2007 |
| WO | 2008026999 A2 | 3/2008 |
| WO | 2008027000 A2 | 3/2008 |
| WO | 2008026999 A3 | 5/2008 |
| WO | 2009008539 A1 | 1/2009 |
| WO | 2009089059 A2 | 7/2009 |
| WO | 2009089059 A3 | 9/2009 |
| WO | 2010125148 A2 | 11/2010 |
| WO | 2010125148 A3 | 1/2011 |
| WO | WO2011004011 A1 | 1/2011 |
| WO | 2012093132 A1 | 7/2012 |
| WO | 2013024074 A1 | 2/2013 |
| WO | 2014070983 A1 | 5/2014 |
| WO | 2014138906 A1 | 9/2014 |
| WO | 2016095013 A1 | 6/2016 |
| WO | 2017077380 A1 | 5/2017 |
| WO | 2017101867 A1 | 6/2017 |
| WO | 2017101868 A1 | 6/2017 |
| WO | 2017101869 A1 | 6/2017 |
| WO | 2017101871 A1 | 6/2017 |
| WO | WO2018107684 A1 | 6/2018 |
| WO | WO2018107685 A1 | 6/2018 |
| WO | WO2018107688 A1 | 6/2018 |
| WO | WO2018107692 A1 | 6/2018 |
| WO | WO2018107707 A1 | 6/2018 |
| WO | WO2018108161 A1 | 6/2018 |
| WO | 2018234861 A1 | 12/2018 |

OTHER PUBLICATIONS

NCBI BLAST results for SEQID No. 2 and 6, ran on Oct. 21, 2021 5 pages (Year: 2021).*

Crandall, D.L. et al. (Oct. 20006, e-pub. Jul. 6, 2006). "Modulation of Adipose Tissue Development by Pharmacological Inhibition of PAI-1," Arterioscler Thromb Vasc Biol. 26(10): 2209-2215.

International Search Report, dated Sep. 14, 2017, PCT Application No. PCT/CN2017/089043, 7 pages.

International Search Report, dated Sep. 8, 2017, PCT Application No. PCT/CN2017/089044, 7 pages.

International Search Report, dated Sep. 8, 2017, PCT Application No. PCT/CN2017/089045, 7 pages.

Jiang, G. et al. (Dec. 31, 1991). "Research Progress Of Antithrombotic and Thrombolytic Drugs," Chinese Journal of Biochemical and Pharmaceutics. 1:1-4. English Abstract.

Ma, D. et al. (Aug. 10, 1994). "Molecular Relations Between Thrombosis and Atherosclerosis," Cerebrovascular Diseases Foreign Medical Sciences 2(4):195-197. English Abstract.

Mehta, J. L. et al. (Mar. 1, 1995). "Recombinant Lys-Plasminogen, but Not Glu-Plasminogen, Improves Recombinant Tissue-Type Plasminogen Activator-Induced Coronary Thrombolysis in Dogs," Journal of the American College of Cardiology 25(3):753-760.

Wu, M. et al. (May 15, 2007). "Research of Relationship Between Postprandial Hyperlipidemia, Carotid Atherosclerosis and Fibrinolytic Activity In Patients With Type 2 Diabetes Mellitus," Journal of Shandong University Health Science 45(5):503-506. English Abstract.

Xiao, Q. et al. (Sep. 1997). "Plasminogen Deficiency Accelerates Vessel Wall Disease In Mice Predisposed To Atherosclerosis" Proceedings of the National Academy of Sciences 94:10335-10340.

Yang, S. et al. (Mar. 30, 2002). "Coronary Angiographic Analysis Of Coronary Heart Disease Complicated With Type 2 Diabetes," Practical Journal of Medicine & Pharmacy 19(3):164 and 165. English Equivalent Abstract Only.

Ye, P. et al. (Dec. 31, 1998). "The Association of Hypertriglyceridemia with Plasma Haemostatic and Fibrinolytic Activities," Chinese Journal of Arteriosc Lerosis. 6(4):333-335. English Abstract.

Yin, G. et al. (Feb. 28, 2005). "Expression and Purification Of The Gene Clone Of Human Plasminogen Kringle5 Region," Academic Journal of Shanghai Second Medical University 25(02):151-154. English Abstract.

Written Opinion of the International Searching Authority dated Sep. 14, 2017, PCT Application No. PCT/CN2017/089043, 5 pages.

Written Opinion of the International Searching Authority dated Sep. 8, 2017, PCT Application No. PCT/CN2017/089044, 5 pages.

Written Opinion of the International Searching Authority dated Sep. 8, 2017, PCT Application No. PCT/CN2017/089045, 5 pages.

(56) References Cited

OTHER PUBLICATIONS

U.S. Appl. No. 16/469,611, Jinan, L. filed Jun. 13, 2019.
U.S. Appl. No. 16/470,160, Jinan, L. filed Jun. 14, 2019.
U.S. Appl. No. 16/469,168, Jinan, L. filed Jun. 13, 2019.
U.S. Appl. No. 16/470,173, Jinan, L. filed Jun. 14, 2019.
U.S. Appl. No. 16/470,174, Jinan, L. filed Jun. 14, 2019.
Abe, T. (1981). "Progress of Thrombolytic Therapy and its Clinical Effect," Blood And Vessel 12(4):493-501. English Abstract.
Aisina, R.B. et al. (2014). "Structure and Function of Plasminogen/Plasmin System," Russian Journal of Bioorganic Chemistry 40(6):590-604.
Alessi, M. C. et al. (Aug. 24, 2006). "PAI-1 And The Metabolic Syndrome: Links, Causes, And Consequences," Arterioscler Thromb Vasc Biol. 26(10):2200-2207.
Anderle, K. et al. (1988). "Review of Studies with Plasminogen Concentrates and Proposals for Further Therapeutic Strategies with Plasminogen Concentrates," Heamostasis 18(Suppl.1):165-175.
Badylak, S.F. (1991). "Enhancement Of The Thrombolytic Efficacy Of Prourokinase By Lys-Plasminogen In A Dog Model Of Artbrial Thrombosis," Thrombosis Research 62:115-126.
Beier, J.I. et al. (Jan. 31, 2012). "Alcoholic Liver Disease and the Potential Role Of Plasminogen Activator Inhibitor-1 and Fibrin Metabolism," Exp. Biol. Med. 237(1):1-9, 19 pages.
Bezerra, J.A. et al. (Dec. 21, 1999). "Plasminogen Deficiency Leads To Impaired Remodeling After A Toxic Injury To The Liver," PNAS 96(26):15143-15148.
Bhatt, H.B. et al. (2015). "Fatty Liver Disease in Diabetes Mellitus," HepatoBiliary Surg. Nutr. 4(2):101-108.
Biosis (2002). Accession No. 2002-354449, 1 page.
Bookstein, J.J. MD et al. (2000). "Plasminogen-Enriched Pulse-Spray Thrombolysis With tPA: Further Developments, " Journal of Vascular and Interventional Radiology 11(10):1353-1362.
CDC (Oct. 3, 2017). "CDC. Cancers Associated With Overweight And Obesity Make Up 40 Percent Of Cancers Diagnosed in the United States," Press Release Retrieved from Internet https://www.cdc.gov/media/releases/2017/p1003-vs-cancer-obesity.html, 3 pages.
Chang, P.C. et al. (Jan. 1, 2010). "Human Plasminogen Kringle 1-5 Reduces Atherosclerosis and Neointima Formation In Mice By Suppressing The Inflammatory Signaling Pathway," Journal Of Thrombosis and Haemostasis 8(1):194-201.
Chen, W.-P. et al. (Sep. 30, 2009). "Effects of Fibrate on the Pathophysiology of Kidney," International Journal of Endocrinology and Metabolism 29(5):332-334. English Abstract.
Corvera, S. et al. (Mar. 2014). "Adipose Tissue Angiogenesis: Impacton Obesity and Type-2 Diabetes," Biochim. Biophys Acta. 1842(3):463-472, 23 pages.
Danese, C. et al. (No Date). "Lipoproteina(a)e plasminogeno nella malattia aterosclerotia," Minervacardioangiologica 44(11):529-533. English Abstract Only.
Feuerstein, G.Z. et al. (1995). "Cardioprotection and Thrombolysis by Anistrephase in Anesthetized Dogs," Journal of Cardiovascular Pharmacology 25:625-633.
Genbank (Mar. 15, 2015). NP-000292.1, "Plasminogen Isoform 1 Precursor [*Homo sapiens*]", 5 pages.
Getz, G.S. et al. (2010). "HDL Apolipoprotein-Related Peptides in the Treatment of Atherosclerosis and Other Inflammatory Disorders," Curr. Pharm. Des 16(28):3173-3184, 21 pages.
Harvard (Feb. 2012). "What to Do About Nonalcoholic Fatty Liver Disease," Harvard Health Publishing, 4 pages.
Jia, A. et al. (Oct. 2013). "Evaluation of Fibrinolytic Enzyme In Treatment of Diabetic Cerebral Infarction," Int. J Lab Med. 34(19):2614-2616. English Abstract, 4 pages.
Kaji, H. (Oct. 31, 2016). "Adipose Tissue-Derived Plasminogen Activator Inhibitor-1 Function and Regulation," Comprehensive Physiology 6:1873-1896.
Kawao, N. et al. (2010, e-pub. Jan. 10, 2010). "Role of Plasminogen in Macrophage Accumulation During Liver Repair," Thrombosis Research 125:e214-e221.

Kopec, A.K. et al. (Jun. 2016, e-pub. May 4, 2016). "Role of Fibrin(ogen) in Progression of Liver Disease: Guilt by Association?" Semin Thromb Hemost. 42(4):397-407, 18 pages.
Kunadian, V. et al. (Apr. 1, 2012). "Thrombolytic and Myocardial Infarction," Cardiovascular Therapeutics 30(2):e81-e88.
Li, L.-Y. et al. (Mar. 1, 2005). "Angiopoietins and Tie2 In Health and Disease," Pediatric Enoocrinology Reviews 2(3):399-408.
Li, Q. (Apr. 26, 2011). "Research Progress On Pathogenesis Of Diabetic Heart Disease (DC)," Chinese J. General Practice 9(2):291-311, English Abstract, 3 pages.
Li, Z. et al. (Apr. 30, 2006). "Research Progress of Liver Fibrosis Treatment," Journal of Liaoning Medical College 28(2):46-48.
Lijnen, H. R. et al. (2007, e-pub. Aug. 23, 2007). "Angiogenesis and Obesity," Cardiovascular Research 78(2):286-293.
Lingohr, M.K. et al. (Jun. 9, 2006). "Specific Regulation of IRS-2 Expression By Glucose In Rat Primary Pancreatic Islet β-Cells," The Journal of Biological Chemistry 281(23):15884-15892.
Lipek, T. et al. (May 2015). "Obesogenic Environments: Environmental Approaches To Obesity Prevention," J Pediatr Endocrinol Metab. 28(5-6):485-495.
Liu, J.Y. (2014, e-pub. Oct. 28, 2014). "Ethanol and Liver: Recent Insights Into The Mechanisms Of Ethanol-Induced Fatty Liver," World J. Gastroenterol, 20(40):14672-14685.
Liu, X. (Nov. 2014). "The Study of Plasmin Combined With Atorvastatin In The Treatment of Cerebral Infarction Patients With Hyperlipidemia," Modern Journal of Integrated Traditional Chinese and Western Medicine 23(31):3490-3491. English Abstract.
Liu, M.Y. et al. (Oct. 31, 2010). "Plasminogen: Structure, Function and Evolution," Journal Of Ocean University Of China 40(10):69-74. English Abstract.
Ma, L.-J. et al. (Feb. 2004). "Prevention of Obesity and Insulin Resistance in Mice Lacking Plasminogen Activator Inhibitor 1," Diabetes 53:336-346.
Ma, R. et al. (Aug. 6, 2002). "Adipose Tissue Mass Can Be Regulated Through The Vasculature," PNAS 99(16):10730-10735.
Mayo Clinic (1998). "Heart Attack 1998-2020," 4 pages.
Miles L.A et al. (Nov. 11, 2016). "Abstract 19088 the Plasminogen Receptor,Plg-Rkt, Regulates Metabolic Homeostasis and Promotes Healthy Adipose Function," Circulation 134(Suppl 1):A19088, 6 pages.
Mitchell, J.W. et al. (Jun. 1, 2006). "Plasminogen Inhibits TNF α-Induced Apoptosis In Monocytes," Blood 107(11):4383-4390.
Morishita, R. et al. (1988). "Novel Therapeutic Atrategy for Atherosclerosis: Ribozyme Oligonucleotides Against Apolipoprotein(a) Selectively Inhibit Apolipoprotein(a) But Not Plasminogen Gene Expression," Circulation 98:1898-1904.
Naitou, G. (1986). "The Formulation and Clinical Experience of Plasminogen Activator System," Journal of Japan Society of Blood Transfusion 32(6):590-593. English Abstract.
Neubauer et al. (Apr. 1995). "Accumulation and Cellular Localization Of Fibrinogen/Fibrin During Short-Term And Long-Term Rat Liver Injury," Gastroenterology 108(4):1124-1135.
Obesity Harvard (2016). "Fatty Liver Disease and Your Heart," Harvard Health Publishing 3 pages.
Ogru, O. et al. (2016). "Type 2 Oral Diabetes Medications," MedicineNet.com, 4 pages.
Okada, K. et al. (Sep. 2008). "Binding of Plasminogen To Hepatocytes Isolated From Injured Mice Liver and Nonparenchymal Cell-Dependent Proliferation Of Hepatocytes," Blood Coagulation and Fibrinolysis 19:503-511.
Peng, Y. et al. (Dec. 31, 2005). "Protective Effects of Recombinant Tissue Plasminogen Activator on Acute Myocardial Infarction in Senile Rats," Chinese Journal of Gerontology 25(12):1517-1518. English Abstract.
Pohl, J.F. et al. (Dec. 2001). "Plasminogen Deficiency Leads to Impaired Lobular Reorganization and Matrix Accumulation after Chronic Liver Injury," American Journal of Pathology 159(6):2179-2186.
Qureshi, K. et al. (Jul. 14, 2007). "Metabolic Liver Disease of Obesity and Role of Adipose Tissue in the Pathogenesis of Nonalcoholic Fatty Liver Disease," WJG 13(26):3540-3553.

(56) References Cited

OTHER PUBLICATIONS

Schmitz, V. et al. (2007). "Plasminogen Fragment K1-5 Improves Survival In A Murine Hepatocellular Carcinoma Model," Gut 56:271-278.
Science Daily (2008). "How Diabetes Drives Atherosclerosis" 2 pages.
Sha, J. et al. (Mar. 22, 2002). "Plasminogen Reduces Atherosclerosis In Apo(a) Transgenic Mice," Annual Meeting of Professional Research Scientiste On Experimental Biology 16(5):A823.
Shanmukhappa, K. et al. (May 8, 2009). "Plasmin-Mediated Proteolysis Is Required For Hepatocyte Growth Factor Activation During Liver Repair," The Journal Of Biological Chemistry 284(19):12917-12923.
Shen, Y. et al. (Jun. 14, 2012). "Plasminogen is a Key Proinflammatory Regulator That Accelerates the Healing of Acute and Diabetic Wounds" Thrombosis and Hemostasis, 119(24):5878-5887.
Sima, J. et al. (Apr. 23, 2004, e-pub. Mar. 23, 2004). "The Effect Of Angiostatin On Vascular Leakage and VEGF Expression In Rat Retina," FEBS Letters 564(1-2):19-23.
Sundell, I.B. (Aug. 5, 1997). "Reduction in Steant and Vascular Graft Thrombosis and Enhancement of Thrombolysis by Recombinant Lys-Plasminogen in Nonhuman Primates," Circulation 96(3):941-948, 27 pages.
Tahara, M. et al. (1999). "Hepatocyte Growth Factor Leads To Recovery From Alcohol-Induced Fatty Liver In Rats," J Clin Invest. 103(3):313-320.
Takamura T. et al., (Mar. 26, 2004). "Genes For Systemic Vascular Complications Are Differentially Expressed In The Lives Of Type 2 Diabetic Patients," Diabetologia 47:638-647.
Tanaka, K. et al. (2000). "Involvement Of Tissue Line System In Liver Regenerating: Examination Using Plasminogen Gene Knockout Mice," Journal of Japan Surgical Society 101:520.
Tsuchida, I. (1981). "Effect Of Urokinase On Heart and Brain Infarctions Combined With Diabetic Patients," Clinical and Research 58(2):659-666. English Abstract.
UCSD (2021). "Nonalchoholic Fatty Liver Disease," UC San Diego Health Wayback Machine 2 pages.
Uniprot Protein Database Blast Results, Human Plasminogen Amino Acids 581-808 accessed on Aug. 23, 2020, 5 pages.
Vogten, J.M. et al. (2004, e-pub. Jan. 10, 2004). "Angiostatin Inhibits Experimental Liver Fibrosis In Mice," International Journal Of Colorectal Disease 19(4):387-394.
Wang, G. (Aug. 31, 2007). "Effects of Actilyse on Hemorheology in Rats with Acute Ischemic Myocardial Injure," Chinese Journal of Cardiovascular Rehabilitation Medicine 16(4):369-371, English Abstract.
Wang, L. et al. (Nov. 30, 2004). "Protective Effects of rt-PA on Experimental Myocardial Ischemia in Rats," Journal of Cardiovascular and Pulmonary Diseases 23(4):238-239, English Abstract.
Xu, D. (Feb. 2012). "Therapeutic Effect Of Recombinant Tissue Plasminogen Activator On Acute Cerebral Infarction," Prevention and Treatment of Cerebral-Vascular Disease 12(1):37-39.
Xu, L. et al. (Aug. 1, 2012). "Diabetic Angiopathy and Angiogenic Defects," Fibrogenesis & Tissue Repair 5(1):13. 9 pages.
Yang, L. et al. (2004). "Changes of Fbrinolytic Parameters in Coronary Heart Disease," Chinese Journal of Thrombosis and Hemostasis 10(1):8-10. English Abstract.
Zhang, S.X. et al. (Jan. 4, 2006). "Therapeutic Potential of Angiostatin in Diabetic Nephropathy," J. Am. Soc. Nephrol. 17:475-486, 12 pages.
Zhang, Y. et al. (Apr. 30, 2005). "Fibrinolytic Activity and Type 2 Diabetes Mellitus and Macroangiopathy Thereof," Foreign Medical Sciences 25:42-44. English Abstract.
Haka, A.S. et al. (2013) "Plasmin Promotes Foam Cell Formation By Increasing Macrophage Catabolism of Aggregated Low-Density Lipoprotein," Arterioscler Thromb. Vasc. Biol. 33:1768-1778.
Kremen, M. et al. (Nov. 4, 2008). "Plasminogen Mediates the Atherogenic Effects of Macrophage-Expressed Urokinase and Accelerates Atherosclerosis in apoE-Knockout Mice," PNAS 105(44):17109-17114.

* cited by examiner

METHOD FOR TREATING CORONARY ATHEROSCLEROSIS AND COMPLICATIONS THEREOF

CROSS REFERENCE TO RELATED APPLICATIONS

This application is a National Phase application under 35 U.S.C. § 371 of International Application No. PCT/CN2017/089044, filed Jun. 19, 2017, which claims priority to International Application No. PCT/CN2016/110168, filed Dec. 15, 2016, and International Application No. PCT/CN2016/110172, filed Dec. 15, 2016, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922000500SEQLIST.TXT, date recorded: Jun. 7, 2019, size: 46 KB).

TECHNICAL FIELD

The present invention relates to the role of plasminogen in preventing and/or treating atherosclerosis and its related conditions, thereby providing a novel therapeutic strategy for preventing and/or treating atherosclerosis and its related conditions.

BACKGROUND ART

Atherosclerosis (AS) is the main cause of coronary heart disease, cerebral infarction, and peripheral vascular disease. Lipid metabolism disorder is the pathological basis of atherosclerosis, wherein the lesion of affected artery begins from intima, where accumulation of lipids and compound carbohydrates, hemorrhage and thrombosis first appear generally, followed by hyperplasia of fibrous tissue and calcinosis, with gradual metamorphosis and calcification of the arterial medial layer, leading to thickening and hardening of the arterial wall, and stenosis of vascular lumen. The lesion generally involves the large and medium muscular arteries. Once the lesion has developed enough to block the arterial lumen, the tissues or organs supplied by the artery will become ischemic or necrotic.

Atherosclerosis is the common pathological basis of various cardiovascular and cerebrovascular diseases, and also the most common disease of cardiovascular system diseases, which seriously endangers human health. The development and progression of atherosclerosis comprises lipid invasion, platelet activation, thrombosis, intimal injury, inflammatory response, oxidative stress, vascular smooth muscle cell (VSMC) activation, selective matrix metabolism, vascular remodeling, etc. [1] Although through nearly a century of research, many scholars have also proposed different theories about the pathogenesis of AS, such as lipid infiltration theory, macrophage receptor loss theory, smooth muscle mutation theory, injury response theory, inflammatory response theory, hemodynamic theory, and immunological theory, no single theory can fully explain the development and progression of AS. In recent years, a large number of experimental research data at the cellular and molecular level have expanded people's understanding of the normal hemeostasis of endothelial cells, VSMCs, mononuclear macrophages, and platelets, so as to further understand their roles in the formation and pathogenesis of AS.

1. Role of Vascular Endothelial Cell Injury

Studies have found that vascular endothelial dysfunction has been formed long before the appearance of atherosclerotic plaques. Esper et al. [2] reported that endothelial cells can produce a large number of molecules with bidirectional function, which can balance the promoting and inhibiting effects. When endothelial cells lose their ability to maintain such delicate balance, lipids and white blood cells (mainly monocytes and T lymphocytes) would invade the endothelium, triggering an inflammatory response and the formation of fatty streaks. Dysfunction, activation and morphological injury of endothelial cells can trigger changes in monocytes and platelets in blood, and VSMCs at the tunica media of vascular walls to eventually form AS. The specific mechanism is as follows: (1) increased permeability of endothelial cells is the main initial link of AS, and the earliest pathological change of lipids entering the subendothelium of arterial wall [3]; (2) the adhesion of platelets and monocytes is increased, Ott et al. [4] reported that the increased expression of cell adhesion molecules on the surface of a dysfunctional endothelial cell may promote the adhesion of monocytes, thus promoting monocytes containing bacteria to infiltrate into the AS plaques from circulating blood; and (3) a variety of growth factors are secreted, such as monocyte chemoattractant protein 21 (MPC21), fibroblast growth factor, transforming growth factor (TGF), platelet-derived growth factor (PDGF), etc., so as to attract monocytes to aggregate and adhere to the endothelium, migrate into the subendothelial space, and ingest a large amount of lipids oxidized under the intima through the mediation of scavenger receptor, CD36 receptor and Fc receptor on the surface to form monocyte-derived foam cells. Boos et al. [3] pointed out that the extent of endothelial injury can be used as a new onset indicator of the pathogenesis and severity of AS to some extent.

2. Role of Platelets

After the injury of arterial endothelial cells, it can promote the adhesion of platelets to the injured endothelial cells, thereby promoting the release of PDGF, leading to the continuous proliferation of myointimal cells, and eventually leading to collagen synthesis and the formation of AS plaques. In the final stage of AS thrombosis, the adhesion, activation and aggregation of platelets can lead to arterial occlusion and secondary ischemia [5]. Platelets interact with endothelial cells and connective tissues, which is important for the development of AS on local vascular walls. The role of platelets in AS is mainly manifested in the following aspects: (1) Endothelial injury in any form can cause a large number of platelets to adhere to and aggregate at the local endothelium, activate the coagulation system, and lead to thrombosis. (2) Secreted and released various active substances, such as PDGF, platelet factor 4, and β-thromboglobulin, have a strong chemotactic effect on VSMCs and monocytes, participate in migration and proliferation of VSMCs and modification of aortic intima, and attract monocytes to adhere to endothelium. Some scholars pointed out that PDGF has chemotactic effect on fibroblasts and promotes the generation of individual antigenic determinants of monocytes, which plays an important role in the formation of AS. (3) Venous endothelial cells can produce nitric oxide and prostacyclin, which are constantly released in the lungs to regulate platelet function.

3. Role of Lipids in the Development and Progression of Atherosclerosis

A large number of studies have demonstrated that the pathological changes of AS are closely related to the blood lipid level, particularly the plasma cholesterol and triacylglycerol levels [6]. Some scholars proposed that the deposition of lipids and fatty acids is an important pathological mechanism of endothelial cell dysfunction and formation of AS. Studies have found that the protein and gene expression of apolipoprotein C1 and apolipoprotein E in arteries with AS plaques is remarkably higher than that in normal arteries, which may be a cause of the formation of AS rather than just a result [7]. It has been recognized that the mechanism of action of hyperlipemia in the pathogenesis of AS, in addition to directly causing endothelial cell injury, is mainly to increase the permeability of endothelial cells, which is related to the oxidative modification of low-density lipoprotein (LDL) to become oxidized low-density lipoprotein (ox-LDL). When ox-LDL passes through the intact endothelium, plasma LDL is transported to the subendothelial space for oxidative modification. LDL induces clearance of macrophages and proliferation of VSMCs at the tunica media to form atheromatous plaques. These changes may ultimately lead to the formation of fatty streaks, fibrous plaques, and/or atheromatous plaques at the arterial intima.

4. Role of Mononuclear Macrophages

Studies have shown that AS plaques contain infiltration of inflammatory response cells including monocytes, monocyte-derived macrophages, macrophages loading ox-LDL (i.e., foam cells), T lymphocytes, etc. [8] The role of mononuclear macrophages in AS can be summarized as follows: (1) phagocytosis: foam cells in the early stage of lesion are mostly derived from monocytes in blood. The latter enters the subendothelium and transforms into macrophages. The specific receptor on surfaces of the macrophages can bind to ox-LDL, thereby the macrophages ingest a large amount of cholesterol and becoming foam cells. (2) Participating in inflammatory response and immune response: the above-mentioned phagocytic process can induce a specific inflammatory response by releasing inflammatory response factors into the extracellular matrix. The infiltration of T lymphocytes can be seen in the lesion of AS, and the fibrous cap of a ruptured AS plaque contains more macrophages than that of a non-ruptured plaque. (3) Participating in proliferation response: when activated, macrophages can release a variety of cytokines and growth factors, which promote the migration and proliferation of VSMCs at the tunica media. Furthermore, macrophages express a variety of metalloproteinases and serine proteases, leading to degradation of extracellular matrix, instability of plaques and even a tendency to rupture [9].

5. Role of VSMCs

After several years of research, it has been recognized that the proliferation of VSMCs at the tunica media and migration of them into the intima and the synthesis of matrix proteins are main links involved in the formation of lesions in the progression of AS, and play an important role in the intima thickening of AS and restenosis [10]. The pathogenesis and progression of AS plaques and restenosis involve complex interactions between vascular wall cells, in which cytokines, inflammatory responses, chemokines and growth factors play an important role. The migrating VSMCs mediate phagocytosis of lipids via the LDL receptor on the surface, forming VSMC-derived foam cells which participate in the formation of lesions. Furthermore, these proliferating VSMCs at the intima can also synthesize collagen, elastin, glycoprotein, etc., and macrophages phagocytize LDL and release free lipids, both of which thicken and harden the diseased intima and promote the formation of sclerotic plaques. In this regard, many efforts have been made to inhibit the accumulation of the above-mentioned cells, and great success has been achieved in restenosis after stenting [11].

Diabetes mellitus is closely related to atherosclerosis, which is manifested by early onset, severe degree and poor prognosis of atherosclerosis in diabetic patients, and atherosclerosis is the main cause of death in diabetic patients.

Clinically, it has been found that the pathological changes of coronary arteries in diabetic patients are substantially characterized by more affected vessels, severe coronary artery stenosis, and more diffuse and severe lesions, and that the mechanism is mostly attributed to abnormal glucose metabolism causing atherosclerosis. With further in-depth research, more results indicate that diabetes mellitus-induced atherosclerosis is not caused by a single factor, but through a variety of pathways and more complex mechanisms to induce and promote the development and progression of atherosclerosis, such as polarization of macrophages, macrophage migration inhibitory factor pathway, advanced glycation end products pathway, scavenger receptor upregulation, insulin resistance, ubiquitin proteasome system (UPS) activation, and platelet-derived growth factor (PDGF) activation pathway. [12]

In patients with type 2 diabetes mellitus, the polarization of macrophages is out of balance in tissues such as white fat, which is manifested by increased M1-type macrophages. M1-type macrophages mainly secrete TNF-α, IL-6, monocyte chemoattractant protein 1, etc., which exert a pro-inflammatory effect. The above-mentioned cytokines not only induce insulin resistance but also promote atherosclerosis [13].

Macrophage migration inhibitory factor (MIF) is an important factor involved in immune and inflammatory responses. In diabetic patients, increased expression of MIF may be associated with atherosclerosis complicated with diabetes mellitus [14]. The mechanism of inducing atherosclerosis is as follows: (1) MIF make macrophages infiltrate and activated at inflammatory sites, thereby accelerating lipid phagocytosis, and inducing the formation of foam cells. Studies have found that the uptake of oxidized low-density lipoprotein by macrophages up-regulates MIF, and accordingly MIF can increase the uptake of oxidized low-density lipoprotein and promote the formation of foam cells. (2) MIF can activate vascular endothelial cells and smooth muscle cells to express monocyte chemoattractant protein 1 and intercellular adhesion molecule 1, respectively, and increase the chemotactic migration of mononuclear macrophages, thus accelerating atherosclerosis. The use of anti-MIF antibody in various arterial models can weaken the markers for the activation of subendothelial macrophages, foam cells, and macrophages.

Advanced glycation end products (AGEs) can promote the development and progression of atherosclerosis in diabetic patients. AGEs, as non-enzymatic glycosylation products of glucose with proteins and lipoproteins in the arterial walls, can bind to the corresponding receptors to accelerate atherosclerosis through the following mechanisms: (1) long-term hyperglycemia can increase the production of AGEs. AGEs can modify proteins, nucleic acids and lipids, increase the production of reactive oxygen species and enhance oxidative stress. AGEs can increase NADPH oxidase activity of neutrophils while increasing the production of oxygen free radicals in neutrophils, and can thus promote vascular oxidative stress, and increase the incidence of cardiovascular disease in diabetic patients [15]. (2) AGEs increase the expression of adhesion molecules, and the AGE receptors on the surface of myeloid and non-myeloid cells can increase the expression of vascular adhesion molecule 1, accelerating the atherosclerosis associated with diabetes mellitus [16].

Insulin resistance (IR) means that the sensitivity and responsiveness of tissues targeted by insulin are decreased to exogenous or endogenous insulin. Type 2 diabetes mellitus is generally complicated with insulin resistance. Insulin resistance can accelerate atherosclerosis in diabetes mellitus through the following mechanisms: (1) insulin resistance accelerates macrophage apoptosis: studies have found that the core of atherosclerotic plaques in the progressive stage in diabetic patients is remarkably larger than that in non-diabetic patients [17]. In the atherosclerotic lesions in the progressive stage of diabetes mellitus, apoptosis induced by endoplasmic reticulum stress is remarkably increased due to the insulin resistance of macrophages, promoting the enlargement of plaque core. (2) CX3CL1/CX3CL1 axis activation is found remarkably increased in patients with insulin resistance and metabolic syndrome, which is positively correlated with accelerated atherosclerosis. Activation of the axis has been found to increase instability of plaques in animal models. Insulin resistance accelerates atherosclerosis by activating the CX3CL1/CX3CL1 axis and inducing apoptosis of vascular smooth muscle cells [18]. The knockout of vitamin D3 receptor in macrophages promotes insulin resistance and accelerates atherosclerosis [19].

Enhanced endogenous oxidative stress in diabetic patients leads to excessive activation of UPS of macrophages [20]. The excessive activation of UPS promotes the expression and secretion of inflammatory factors (such as vascular cell adhesion factor 1 and intercellular adhesion molecule 1) in diabetes mellitus, causing irreversible injury of vascular endothelial cells and resulting in atherosclerosis [21].

In addition, in diabetic patients, AGEs, angiotensin II, endothelin, inflammation and hyperlipemia state increase the activity of PDGF pathway, and the increased activity of PDGF pathway can promote the inflammatory response. PDGF can up-regulate the expression of connective tissue growth factor, promoting the migration, adhesion and proliferation of endothelial cells and fibroblasts, and thus aggravating the development of atherosclerosis [22].

So far, the drug therapies for atherosclerosis mainly comprise a hypolipidemic drug, an anti-platelet drug, an antihypertensive drug, a vasodilator, a hypoglycemic drug, an anticoagulant drug, and a thrombolytic drug. In the studies, surprisingly, we find that plasminogen can alleviate lipid accumulation and deposition on the arterial walls, reduce fibrous tissue hyperplasia, repair an injury of vascular walls caused by atherosclerosis, and improve an ischemic injury of a tissue or organ caused by atherosclerosis, and related conditions caused by tissue and organ ischemia.

SUMMARY OF THE INVENTION

The present invention relates to the prevention and/or treatment of coronary atherosclerosis and its related conditions in a subject.

In one aspect, the present invention relates to a method for preventing and/or treating coronary atherosclerosis and its related conditions in a subject, comprising administering a prophylactically and/or therapeutically effective amount of plasminogen to the subject, wherein the subject suffers from, is suspected of suffering from coronary atherosclerosis and its related conditions, or has a risk of suffering from coronary atherosclerosis and its related conditions. The present invention further relates to the use of plasminogen for preventing and/or treating coronary atherosclerosis and its related conditions in a subject. The present invention further relates to the use of plasminogen in the preparation of a medicament, a pharmaceutical composition, an article of manufacture, and a kit for preventing and/or treating coronary atherosclerosis and its related conditions in a subject. Furthermore, the present invention also relates to the plasminogen for preventing and/or treating coronary atherosclerosis and its related conditions in a subject. The present invention further relates to a medicament, a pharmaceutical composition, an article of manufacture, and a kit comprising plasminogen which are useful for preventing and/or treating coronary atherosclerosis and its related conditions in a subject.

In some embodiments, the coronary atherosclerosis-related conditions comprise coronary heart disease, angina pectoris, myocardial infarction, arrhythmia, and heart failure caused by coronary atherosclerosis. In some embodiments, the atherosclerosis is atherosclerosis complicated with diabetes mellitus. In some embodiments, the plasminogen prevents and/or treats atherosclerosis in one or more ways selected from: lowering a serum total cholesterol level in the subject, lowering a serum triglyceride level in the subject, lowering a serum low-density lipoprotein level in the subject, and elevating a serum high-density lipoprotein level in the subject. In some embodiments, the plasminogen prevents and/or treats coronary atherosclerosis by reducing lipid deposition on the arterial wall of a subject. In some embodiments, the plasminogen prevents and/or treats coronary atherosclerosis in one or more ways selected from: promoting fat metabolism in the liver, promoting fat transport in the liver, and reducing fat deposition in the liver of the subject.

In another aspect, the present invention relates to a method for preventing and/or treating an ischemic injury of a tissue or organ and its related conditions caused by coronary atherosclerosis in a subject, comprising administering an effective amount of plasminogen to the subject. The present invention further relates to the use of plasminogen for preventing and/or treating an ischemic injury of a tissue or organ and its related conditions caused by coronary atherosclerosis in a subject. The present invention further relates to the use of plasminogen in the preparation of a medicament, a pharmaceutical composition, an article of manufacture, and a kit for preventing and/or treating an ischemic injury of a tissue or organ and its related conditions caused by coronary atherosclerosis in a subject. Furthermore, the present invention also relates to the plasminogen for preventing and/or treating an ischemic injury of a tissue or organ and its related conditions caused by coronary atherosclerosis in a subject. The present invention further relates to a medicament, a pharmaceutical composition, an article of manufacture, and a kit comprising plasminogen which are useful for preventing and/or treating an ischemic injury of a tissue or organ and its related conditions caused by coronary atherosclerosis in a subject.

In some embodiments, the ischemic injury of a tissue or organ in a subject is myocardial injury caused by coronary atherosclerosis. In some embodiments, the related conditions are coronary heart disease, angina pectoris, myocardial infarction, arrhythmia, or heart failure caused by cardiac blood supply insufficiency. In some embodiments, the ischemic injury of a tissue or organ or its related conditions are cerebral ischemic injury or its related conditions. In some embodiments, the conditions are cerebral ischemia, cerebral thrombosis, brain atrophy, cerebral hemorrhage, or cerebral embolism. In some embodiments, the related conditions are renal insufficiency, hypertension, glomerular fibrosis, renal failure or uremia.

In yet another aspect, the present invention relates to a method for preventing and/or treating coronary thrombosis and its related conditions caused by coronary atherosclerosis in a subject, comprising administering an effective amount of plasminogen to the subject. The present invention further relates to the use of plasminogen for preventing and/or treating coronary thrombosis and its related conditions caused by coronary atherosclerosis in a subject. The present invention further relates to the use of plasminogen in the preparation of a medicament, a pharmaceutical composition, an article of manufacture, and a kit for preventing and/or treating coronary thrombosis and its related conditions caused by coronary atherosclerosis in a subject. Furthermore, the present invention also relates to the plasminogen for preventing and/or treating coronary thrombosis and its related conditions caused by coronary atherosclerosis in a subject. The present invention further relates to a medicament, a pharmaceutical composition, an article of manufacture, and a kit comprising plasminogen which are useful for preventing and/or treating coronary thrombosis and its related conditions caused by coronary atherosclerosis in a subject.

In some embodiments, the conditions comprise coronary heart disease, angina pectoris, myocardial infarction, arrhythmia, heart failure, cerebral ischemia, cerebral thrombosis, brain atrophy, cerebral hemorrhage, cerebral embolism, cerebral infarction, renal insufficiency, hypertension, glomerular fibrosis, renal failure, uremia, intestinal necrosis, intermittent claudication, and gangrene.

In yet another aspect, the present invention relates to a method for preventing and/or treating coronary atherosclerosis complicated with diabetes mellitus in a subject, comprising administering an effective amount of plasminogen to the subject. The present invention further relates to the use of plasminogen for preventing and/or treating coronary atherosclerosis complicated with diabetes mellitus in a subject. The present invention further relates to the use of plasminogen in the preparation of a medicament, a pharmaceutical composition, an article of manufacture, and a kit for preventing and/or treating coronary atherosclerosis complicated with diabetes mellitus in a subject. Furthermore, the present invention also relates to the plasminogen for preventing and/or treating coronary atherosclerosis complicated with diabetes mellitus in a subject. The present invention further relates to a medicament, a pharmaceutical composition, an article of manufacture, and a kit comprising plasminogen which are useful for preventing and/or treating coronary atherosclerosis complicated with diabetes mellitus in a subject.

In yet another aspect, the present invention relates to a method for preventing and/or treating coronary atherosclerosis complicated with diabetes mellitus in a subject, comprising administering an effective amount of plasminogen to the subject. The present invention further relates to the use of plasminogen for preventing and/or treating coronary atherosclerosis complicated with diabetes mellitus in a subject. The present invention further relates to the use of plasminogen in the preparation of a medicament, a pharmaceutical composition, an article of manufacture, and a kit for preventing and/or treating coronary atherosclerosis complicated with diabetes mellitus in a subject. Furthermore, the present invention also relates to the plasminogen for preventing and/or treating coronary atherosclerosis complicated with diabetes mellitus in a subject. The present invention further relates to a medicament, a pharmaceutical composition, an article of manufacture, and a kit comprising plasminogen which are useful for preventing and/or treating coronary atherosclerosis complicated with diabetes mellitus in a subject.

In yet another aspect, the present invention relates to a method for preventing and/or treating coronary heart disease, angina pectoris, myocardial infarction, arrhythmia, or heart failure in a diabetic subject, comprising administering an effective amount of plasminogen to the subject. The present invention further relates to the use of plasminogen for preventing and/or treating coronary heart disease, angina pectoris, myocardial infarction, arrhythmia, or heart failure in a diabetic subject. The present invention further relates to the use of plasminogen in the preparation of a medicament, a pharmaceutical composition, an article of manufacture, and a kit for preventing and/or treating coronary heart disease, angina pectoris, myocardial infarction, arrhythmia, or heart failure in a diabetic subject. Furthermore, the present invention also relates to the plasminogen for preventing and/or treating coronary heart disease, angina pectoris, myocardial infarction, arrhythmia, or heart failure in a diabetic subject. The present invention further relates to a medicament, a pharmaceutical composition, an article of manufacture, and a kit comprising plasminogen which are useful for preventing and/or treating coronary heart disease, angina pectoris, myocardial infarction, arrhythmia, or heart failure in a diabetic subject.

In yet another aspect, the present invention relates to a method for preventing and/or treating atherosclerosis and its related conditions in a subject, comprising administering an effective amount of plasminogen to the subject. The present invention further relates to the use of plasminogen for preventing and/or treating atherosclerosis and its related conditions in a subject. The present invention further relates to the use of plasminogen in the preparation of a medicament, a pharmaceutical composition, an article of manufacture, and a kit for preventing and/or treating atherosclerosis and its related conditions in a subject. Furthermore, the present invention also relates to the plasminogen for preventing and/or treating atherosclerosis and its related conditions in a subject. The present invention further relates to a medicament, a pharmaceutical composition, an article of manufacture, and a kit comprising plasminogen which are useful for preventing and/or treating atherosclerosis and its related conditions in a subject.

In some embodiments, the atherosclerosis comprises aortic atherosclerosis, coronary atherosclerosis, cerebral atherosclerosis, renal atherosclerosis, mesenteric atherosclerosis, and lower limb atherosclerosis. In some embodiments, the atherosclerosis-related conditions comprise related conditions caused by tissue and organ ischemia due to atherosclerosis, comprising coronary heart disease, angina pectoris, myocardial infarction, arrhythmia, and heart failure caused by coronary atherosclerosis; cerebral ischemia, cerebral thrombosis, brain atrophy, cerebral hemorrhage, and cerebral embolism caused by cerebral atherosclerosis; renal insufficiency, hypertension, glomerular fibrosis, renal failure, and uremia caused by renal atherosclerosis; postprandial abdominal pain, dyspepsia, constipation, intestinal wall necrosis, and hemafecia caused by mesenteric atherosclerosis; and intermittent claudication, and gangrene caused by lower limb atherosclerosis.

In some embodiments, the atherosclerosis is selected from: coronary atherosclerosis, cerebral atherosclerosis, and renal atherosclerosis. In some embodiments, the atherosclerosis is atherosclerosis complicated with diabetes mellitus.

In some embodiments, the plasminogen prevents and/or treats atherosclerosis in one or more ways selected from: lowering a serum total cholesterol level in the subject, lowering a serum triglyceride level in the subject, lowering a serum low-density lipoprotein level in the subject, and elevating a serum high-density lipoprotein level in the subject. In some embodiments, the plasminogen prevents and/or treats atherosclerosis by reducing lipid deposition on the arterial wall of a subject. In some embodiments, the plasminogen prevents and/or treats atherosclerosis in one or more ways selected from: promoting fat metabolism in the liver, promoting fat transport in the liver, and reducing fat deposition in the liver of the subject.

In yet another aspect, the present invention relates to a method for preventing and/or treating an ischemic injury of a tissue or organ and its related conditions caused by atherosclerosis in a subject, comprising administering an effective amount of plasminogen to the subject. The present invention further relates to the use of plasminogen for preventing and/or treating an ischemic injury of a tissue or organ and its related conditions caused by atherosclerosis in a subject. The present invention further relates to the use of plasminogen in the preparation of a medicament, a pharmaceutical composition, an article of manufacture, and a kit for preventing and/or treating an ischemic injury of a tissue or organ and its related conditions caused by atherosclerosis in a subject. Furthermore, the present invention also relates to the plasminogen for preventing and/or treating an ischemic injury of a tissue or organ and its related conditions caused by atherosclerosis in a subject. The present invention further relates to a medicament, a pharmaceutical composition, an article of manufacture, and a kit comprising plasminogen which are useful for preventing and/or treating an ischemic injury of a tissue or organ and its related conditions caused by atherosclerosis in a subject.

In some embodiments, the ischemic injury of a tissue or organ in a subject is myocardial injury, cerebral injury or renal injury. In some embodiments, the conditions are coronary heart disease, angina pectoris, myocardial infarction, arrhythmia, heart failure, cerebral ischemia, cerebral thrombosis, brain atrophy, cerebral hemorrhage or cerebral embolism, renal insufficiency, hypertension, glomerular fibrosis, renal failure or uremia.

In yet another aspect, the present invention relates to a method for preventing and/or treating arterial thrombosis and its related conditions caused by atherosclerosis in a subject, comprising administering an effective amount of plasminogen to the subject. The present invention further relates to the use of plasminogen for preventing and/or treating arterial thrombosis and its related conditions caused by atherosclerosis in a subject. The present invention further relates to the use of plasminogen in the preparation of a medicament, a pharmaceutical composition, an article of manufacture, and a kit for preventing and/or treating arterial thrombosis and its related conditions caused by atherosclerosis in a subject. Furthermore, the present invention also relates to the plasminogen for preventing and/or treating arterial thrombosis and its related conditions caused by atherosclerosis in a subject. The present invention further relates to a medicament, a pharmaceutical composition, an article of manufacture, and a kit comprising plasminogen which are useful for preventing and/or treating arterial thrombosis and its related conditions caused by atherosclerosis in a subject.

In some embodiments, the conditions comprise coronary heart disease, angina pectoris, myocardial infarction, arrhythmia, heart failure, cerebral ischemia, cerebral thrombosis, brain atrophy, cerebral hemorrhage, cerebral embolism, cerebral infarction, renal insufficiency, hypertension, glomerular fibrosis, renal failure, uremia, intestinal necrosis, intermittent claudication, and gangrene.

In yet another aspect, the present invention relates to a method for preventing and/or treating atherosclerosis complicated with diabetes mellitus in a subject, comprising administering an effective amount of plasminogen to the subject. The present invention further relates to the use of plasminogen for preventing and/or treating atherosclerosis complicated with diabetes mellitus in a subject. The present invention further relates to the use of plasminogen in the preparation of a medicament, a pharmaceutical composition, an article of manufacture, and a kit for preventing and/or treating atherosclerosis complicated with diabetes mellitus in a subject. Furthermore, the present invention also relates to the plasminogen for preventing and/or treating atherosclerosis complicated with diabetes mellitus in a subject. The present invention further relates to a medicament, a pharmaceutical composition, an article of manufacture, and a kit comprising plasminogen which are useful for preventing and/or treating atherosclerosis complicated with diabetes mellitus in a subject.

In some embodiments, the atherosclerosis is selected from one or more of: aortic atherosclerosis, coronary atherosclerosis, cerebral atherosclerosis, renal atherosclerosis, mesenteric atherosclerosis, and lower limb atherosclerosis.

In yet another aspect, the present invention relates to a method for treating hyperlipemia in a subject with diabetes mellitus or atherosclerosis, comprising administering an effective amount of plasminogen to the subject. The present invention further relates to the use of plasminogen for treating hyperlipemia in a subject with diabetes mellitus or atherosclerosis. The present invention further relates to the use of plasminogen in the preparation of a medicament, a pharmaceutical composition, an article of manufacture, and a kit for treating hyperlipemia in a subject with diabetes mellitus or atherosclerosis. Furthermore, the present invention also relates to the plasminogen for treating hyperlipemia in a subject with diabetes mellitus or atherosclerosis. The present invention further relates to a medicament, a pharmaceutical composition, an article of manufacture, and a kit comprising plasminogen which are useful for treating hyperlipemia in a subject with diabetes mellitus or atherosclerosis.

In some embodiments, the subject exhibits one or more of: an elevated serum total cholesterol level, an elevated serum triglyceride level, an elevated serum low-density lipoprotein level, and a lowered serum high-density lipoprotein level. In some embodiments, the hyperlipemia is improved in one or more ways selected from: lowering a serum total cholesterol level in the subject, lowering a serum triglyceride level in the subject, lowering a serum low-density lipoprotein level in the subject, and elevating a serum high-density lipoprotein level in the subject.

In yet another aspect, the present invention relates to a method for preventing or reducing lipid deposition on the arterial wall of a subject, wherein the subject is susceptible to atherosclerosis or has atherosclerosis, and the method comprises administering an effective amount of plasminogen to the subject. The present invention further relates to the use of plasminogen for preventing or reducing lipid deposition on the arterial wall of a subject. The present invention further relates to the use of plasminogen in the preparation of a medicament, a pharmaceutical composition, an article of manufacture, and a kit for preventing or reducing lipid deposition on the arterial wall of a subject. Furthermore, the present invention also relates to the plasminogen for preventing or reducing lipid deposition on the arterial wall of a subject. The present invention further relates to a medicament, a pharmaceutical composition, an article of manufacture, and a kit for preventing or reducing lipid deposition on the arterial wall of a subject.

In some embodiments, the subject susceptible to atherosclerosis is a subject with a primary or secondary fat metabolism disorder. In some embodiments, the subject susceptible to atherosclerosis is a subject with a liver disease, a kidney disease, obesity, hyperlipemia or diabetes mellitus. In some embodiments, the plasminogen is administered in combination with one or more other drugs or therapies required by the subject. In some embodiments, the other drugs comprise: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine. In some embodiments, the drugs comprise hypolipidemic drugs: statins; fibrates; niacin; cholestyramine; clofibrate; unsaturated fatty acids such as Yishouning, Xuezhiping, and Xinmaile; and alginic sodium diester; anti-platelet drugs: aspirin; dipyridamole; clopidogrel; and cilostazol; vasodilators: hydralazine; nitroglycerin, and isosorbide dinitrate; sodium nitroprusside; α1-receptor blockers such as prazosin; α-receptor blockers such as phentolamine; β2-receptor stimulants such as salbutamol; captopril, enalapril; nifedipine, diltiazem; and salbutamol, loniten, prostaglandin, and atrial natriuretic peptide; thrombolytic drugs: urokinase, and streptokinase; tissue-type plasminogen activators; single chain urokinase-type plasminogen activators; and a TNK tissue-type plasminogen activator; and anticoagulant drugs: heparin; enoxaparin; nadroparin; and bivalirudin.

In some embodiments, the plasminogen has at least 75%, 80%, 85%, 90%, 95%, 96%, 97%, 98% or 99% sequence identity with SEQ ID No. 2, 6, 8, 10 or 12, and still has the activity of plasminogen. In some embodiments, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No. 2, 6, 8, 10 or 12, and still has the activity of plasminogen.

In some embodiments, the plasminogen is a protein that comprises a plasminogen active fragment and still has the activity of plasminogen. In some embodiments, the plasminogen is selected from Glu-plasminogen, Lys-plasminogen, mini-plasminogen, micro-plasminogen, delta-plasminogen or their variants that retain the plasminogen activity. In some embodiments, the plasminogen is a natural or synthetic human plasminogen, or a variant or fragment thereof that still retains the plasminogen activity. In some embodiments, the plasminogen is an ortholog of human plasminogen from a primate or a rodent, or a variant or fragment thereof that still retains the plasminogen activity. In some embodiments, the amino acids of the plasminogen are as shown in SEQ ID No. 2, 6, 8, 10 or 12. In some embodiments, the plasminogen is a natural human plasminogen.

In some embodiments, the subject is a human. In some embodiments, the subject is lack of or deficient in plasminogen. In some embodiments, the lack or deficiency is congenital, secondary and/or local.

In some embodiments, the pharmaceutical composition comprises a pharmaceutically acceptable carrier and the plasminogen for use in the above-mentioned method. In some embodiments, the kit may be a preventive or therapeutic kit comprising: (i) the plasminogen for use in the above-mentioned method, and (ii) a means for delivering the plasminogen to the subject. In some embodiments, the means is a syringe or a vial. In some embodiments, the kit further comprises a label or an instruction for use indicating the administration of the plasminogen to the subject to implement any one of the above-mentioned methods.

In some embodiments, the article of manufacture comprising: a container comprising a label; and (i) the plasminogen for use in the above-mentioned methods or a pharmaceutical composition comprising the plasminogen, wherein the label indicates the administration of the plasminogen or the composition to the subject to implement any one of the above-mentioned methods.

In some embodiments, the kit or the article of manufacture further comprises one or more additional means or containers containing other drugs. In some embodiments, the other drugs are selected from a group of: a hypolipidemic drug, an anti-platelet drug, an antihypertensive drug, a vasodilator, a hypoglycemic drug, an anticoagulant drug, a thrombolytic drug, a hepatoprotective drug, an anti-arrhythmia drug, a cardiotonic drug, a diuretic drug, an anti-infective drug, an antiviral drug, an immunomodulatory drug, an inflammatory regulatory drug, an anti-tumor drug, a hormone drug, and thyroxine.

In some embodiments of the above-mentioned method, the plasminogen is administered by systemic or topical route, preferably by the following routes: intravenous, intramuscular, and subcutaneous administration of plasminogen for treatment. In some embodiments of the above-mentioned method, the plasminogen is administered in combination with a suitable polypeptide carrier or stabilizer. In some embodiments of the above-mentioned method, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily.

The present invention explicitly encompasses all the combinations of technical features belonging to the embodiments of the present invention, and these combined technical solutions have been explicitly disclosed in the present application, as if the above technical solutions were individually and explicitly disclosed. In addition, the present invention also explicitly encompasses all the combinations between various embodiments and elements thereof, and the combined technical solutions are explicitly disclosed herein.

DETAILED DESCRIPTION OF EMBODIMENTS

"Atherosclerosis" is a chronic, progressive arterial disease in which the fat deposited in the arteries partially or completely blocks blood flow. Atherosclerosis occurs when the otherwise smooth and solid arterial intima becomes roughened and thickened and is blocked by fat, fibrin, calcium, and cellular debris. Atherosclerosis is a progressive process. When the concentration of lipids in the blood is greatly increased, fatty streaks form along the arterial wall. These streaks can lead to deposits of fat and cholesterol, which attach to the otherwise smooth arterial intima and thus form nodules. Underneath these nodules, fibrotic scar tissue develops, leading to calcium deposition. The calcium deposits gradually develop into a chalky hard film (referred to as atherosclerotic plaque) that cannot be removed. This permanent film inside the artery would block the normal expansion and contraction of the artery, which slows the blood flow velocity within the artery, making the blood easy to form clots that block or stop blood flowing through the artery.

In the case of atherosclerosis alone, people do not feel any symptoms. The disease is only discovered when an artery connected to a vital organ in the body is blocked. Symptoms are more pronounced when arteries in the organ are blocked. For instance, people may feel angina pectoris if the cardiac feeding artery is partially blocked; however, if it is completely blocked, it may lead to a heart disease (the death of heart tissue fed by the blocked artery). If atherosclerosis affects the cerebral arteries, people may experience dizziness, blurred vision, syncope, and even a stroke (the death of brain tissue fed by the blocked arteries, resulting in a nerve damage, such as paralysis of a limb controlled by dead brain tissue). Occlusion of arteries to the kidneys may also lead to renal failure. Occlusion of blood vessels to the eyes may lead to blindness. Occlusion of arteries in the extremities may lead to lesions in each limb.

Plasmin is a key component of the plasminogen activation system (PA system). It is a broad-spectrum protease that can hydrolyze several components of the extracellular matrix (ECM), including fibrin, gelatin, fibronectin, laminin, and proteoglycan [23]. In addition, plasmin can activate some pro-matrix metalloproteinases (pro-MMPs) to form active matrix metalloproteinases (MMPs). Therefore, plasmin is considered to be an important upstream regulator of extracellular proteolysis [24,25]. Plasmin is formed by the proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. The activity of PAs is simultaneously inhibited by the plasminogen activator inhibitor-1 (PAI-1) of uPA and tPA and regulated by the plasminogen activator inhibitor-2 (PAI-2) that primarily inhibits uPA. There are uPA-specific cell surface receptors (uPARs) that have direct hydrolytic activity on certain cell surfaces [26,27].

Plasminogen is a single-stranded glycoprotein composed of 791 amino acids and has a molecular weight of about 92 kDa [28,29]. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids [30,31]. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease [32]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered plasminogen is a 38 kDa fragment, comprising kringles 1-4, is a potent inhibitor of angiogenesis. This fragment is named as angiostatin and can be produced by proteolysis of plasminogen by several proteases.

The main substrate of plasmin is fibrin, and the dissolution of fibrin is the key to prevent pathological thrombosis [33]. Plasmin also has substrate specificity for several components of ECM, including laminin, fibronectin, proteoglycan and gelatin, indicating that plasmin also plays an important role in ECM remodeling [29,34,35]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis [36]. In addition, plasmin has the ability to activate certain potential forms of growth factors [37-39]. In vitro, plasmin can also hydrolyze components of the complement system and release chemotactic complement fragments.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No. 4) of the natural human plasminogen containing a signal peptide, is a glycoprotein composed of 810 amino acids, which has a molecular weight of about 90 kD and is synthesized mainly in the liver and capable of circulating in the blood; and the cDNA sequence encoding this amino acid sequence is as shown in SEQ ID No. 3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No. 1; and the amino acid sequence is as shown in SEQ ID No. 2. In vivo, Lys-plasminogen, which is formed by hydrolysis of amino acids at positions 76-77 of Glu-plasminogen, is also present, as shown in SEQ ID No. 6; and the cDNA sequence encoding this amino acid sequence is as shown in SEQ ID No. 5. δ-plasminogen is a fragment of full-length plasminogen that lacks the structure of Kringle 2-Kringle 5 and contains only Kringle 1 and the serine protease domain [40,41]. The amino acid sequence (SEQ ID No. 8) of δ-plasminogen has been reported in the literature [41], and the cDNA sequence encoding this amino acid sequence is as shown in SEQ ID No. 7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid) [42]; the amino acid sequence is as shown in SEQ ID No. 10; and the cDNA sequence encoding this amino acid sequence is as shown in SEQ ID No. 9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid) [43], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No. 12; and the cDNA sequence encoding this amino acid sequence is as shown in SEQ ID No. 11.

In the present invention, "plasmin" is used interchangeably with "fibrinolysin" and "fibrinoclase", and the terms have the same meaning; and "plasminogen" is used interchangeably with "profibrinolysin" and "fibrinoclase zymogen", and the terms have the same meaning.

In the present application, the meaning of "lack" in plasminogen is that the content or activity of plasminogen in the body of a subject is lower than that of a normal person, which is low enough to affect the normal physiological function of the subject; and the meaning of "deficiency" in plasminogen is that the content or activity of plasminogen in the body of a subject is significantly lower than that of a normal person, or even the activity or expression is extremely small, and only through exogenous supply can the normal physiological function be maintained.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID No. 14, or an amino acid sequence having an amino acid sequence identity of at least 80%, 90%, 95%, 96%, 97%, 98% or 99% with SEQ ID No. 14. Therefore, plasminogen of the present invention comprises a protein containing the plasminogen active fragment and still having the plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity, hydrophobicity, etc.). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowly method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues); and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction X/Y×100 wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero JA et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp)

promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (e.g., mammalian cells cultured in cell culture in vitro) can also be used to express and generate the anti-Tau antibody of the present invention (e.g., a polynucleotide encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the subject antibody and the like.

Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or nonionic surfactants, such as TWEENTM, PLURONICSTM or polyethylene glycol (PEG). Preferred lyophilized anti-VEGF antibody formulations are described in WO 97/04801, which is incorporated herein by reference.

The formulations of the invention may also comprise one or more active compounds required for the particular condition to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and γ ethyl-L-glutamic acid (Sidman et al. Biopolymers 22:547(1983)), non-degradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulthydryl residues, lyophilizing from acidic solutions, controlling moisture content, using appropriate additives, and developing specific polymer matrix compositions.

Administration and Dosage

The pharmaceutical composition of the present invention is administered in different ways, for example by intravenous, intraperitoneal, subcutaneous, intracranial, intrathecal, intraarterial (e.g., via carotid), and intramuscular administration.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely.

Articles of Manufacture or Kits

One embodiment of the present invention relates to an article of manufacture or a kit comprising plasminogen of the present invention or plasmin useful in the treatment of angiocardiopathy and its related conditions caused by diabetes mellitus. The article preferably includes a container, label or package insert. Suitable containers include bottles, vials, syringes and the like. The container can be made of various materials, such as glass or plastic. The container contains a composition that is effective to treat the disease or condition of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used to treat the angiocardiopathy and its related conditions caused by diabetes mellitus according to the present invention. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to direct a user of the composition to administer to a patient the plasminogen composition and other drugs for treating an accompanying disease.

EXAMPLES

Example 1

Plasminogen Ameliorates Lipid Plaque Deposition in Aorta of ApoE Atherosclerosis Mice Thirteen 6-week-old male ApoE mice were fed with a high-fat and high-cholesterol diet (Nantong TROPHIC, TP2031) for 16 weeks to induce the hyperlipemia model [47,48], 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 10 days. During the administration, mice continued to be fed with a high-fat and high-cholesterol diet. On Day 11, one mouse from each group was randomly sacrificed. The aortas were fixed in 4% paraformaldehyde for 24 to 48 hours, and dissected for general oil red O staining. The aortas were observed and photographed under a stereo microscope at 7×.

Figure 1:
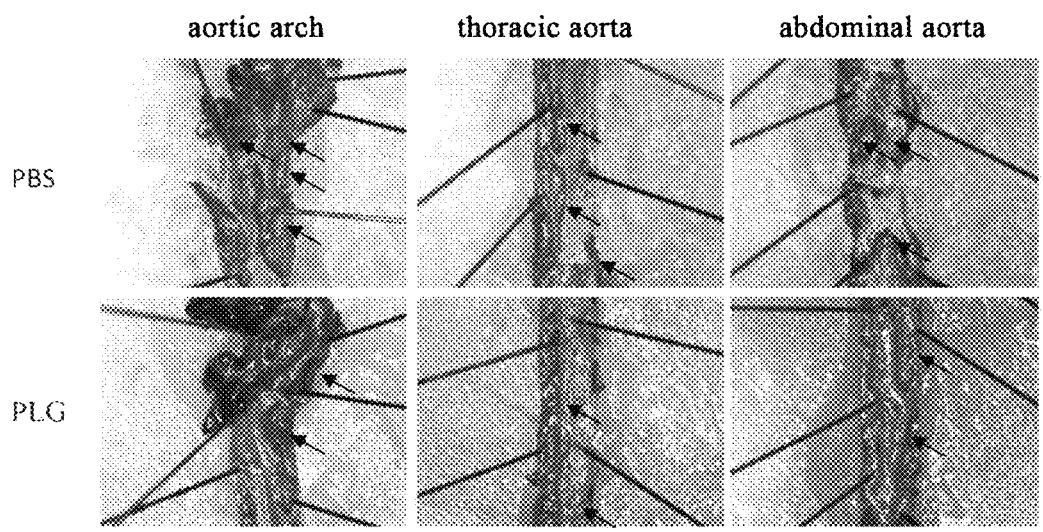
FIG. 1 shows an image of general oil red O staining of aorta after administration of plasminogen to ApoE atherosclerosis model mice for 10 days. The results showed that the area of lipid plaques (indicated by arrow) at the aortic arch, thoracic aorta and abdominal aorta of mice in the group administered with plasminogen was remarkably less than that in the control group administered with vehicle PBS; and the area ratios of lipid to blood vessel were 36.0% in the control group administered with vehicle PBS, and 29.6% in the group administered with plasminogen. It indicates that plasminogen can reduce atherosclerotic plaque deposition in ApoE atherosclerosis model mice, and promote the repair of an atherosclerotic vascular wall injury.

Oil red O staining can show lipid deposition and reflect the severity of injury [49]. The staining results (FIG. 1) showed that the area of lipid plaques (indicated by arrow) at the aortic arch, thoracic aorta and abdominal aorta of mice in the group administered with plasminogen was remarkably less than that in the control group administered with vehicle PBS; and the area ratios of lipid to blood vessel were 36.0% in the control group administered with vehicle PBS, and 29.6% in the group administered with plasminogen. The experiment demonstrates that plasminogen can reduce atherosclerotic plaque deposition in ApoE atherosclerosis model mice, and promote the repair of atherosclerosis.

Example 2

Plasminogen Reduces Lipid Plaque Deposition in Aorta of ApoE Atherosclerosis Mice Thirteen 6-week-old male ApoE mice were fed with a high-fat and high-cholesterol diet (Nantong TROPHIC, TP2031) for 16 weeks to induce the hyperlipemia model [47,48]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 20 days. During the administration, mice continued to be fed with a high-fat and high-cholesterol diet. On Day 21, one mouse from each group was randomly sacrificed. The aortas were fixed in 4% paraformaldehyde for 24 to 48 hours, and dissected for general oil red O staining. The aortas were observed and photographed under a stereo microscope at 7×.

Figure 2:
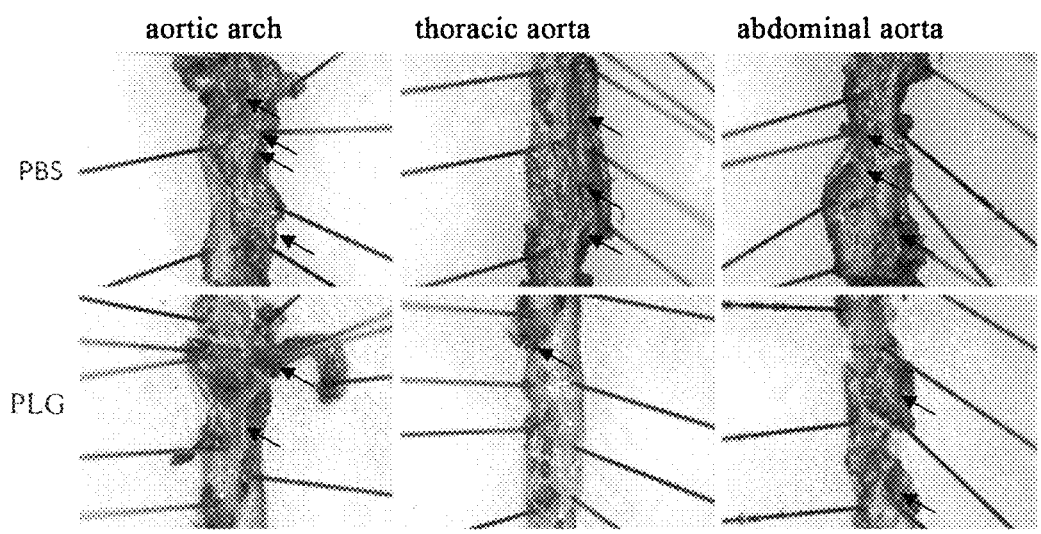
FIG. 2 shows an image of general oil red O staining of aorta after administration of PBS or plasminogen to ApoE atherosclerosis model mice for 20 days. The results showed that the area of lipid plaques (indicated by arrow) at the aortic arch, thoracic aorta and abdominal aorta of mice in the group administered with plasminogen was remarkably less than that in the control group administered with vehicle PBS; and the area ratios of lipid to blood vessel were 48.1% in the control group administered with vehicle PBS, and 39.4% in the group administered with plasminogen. It indicates that plasminogen can reduce atherosclerotic plaque deposition in ApoE atherosclerosis model mice, and promote the repair of an atherosclerotic vascular injury.

The area of lipid plaques (indicated by arrow) at the aortic arch, thoracic aorta and abdominal aorta of mice was remarkably less than that in the control group administered with vehicle PBS; and the area ratios of lipid to blood vessel were 48.1% in the control group administered with vehicle PBS, and 39.4% in the group administered with plasminogen (FIG. 2). It indicates that plasminogen can reduce atherosclerotic plaques in ApoE atherosclerosis model mice, and promote the repair of atherosclerosis.

Example 3

Plasminogen Ameliorates Lipid Deposition in Aortic Sinus of ApoE Atherosclerosis Mice Thirteen 6-week-old male ApoE mice were fed with a high-fat and high-cholesterol diet (Nantong TROPHIC, TP2031) for 16 weeks to induce the hyperlipemia model [47,48]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The hearts were fixed in 4% paraformaldehyde for 24 to 48 hours, then sedimented in 15% and 30% sucrose at 4° C. overnight, respectively, and embedded in OCT. The frozen sections were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 200×.

Figure 3:
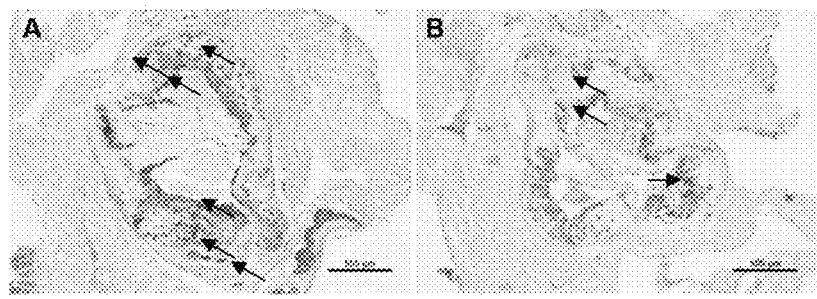
FIG. 3 shows a representative image of oil red O staining of aortic sinus after administration of plasminogen to ApoE atherosclerosis model mice for 30 days. A represents the control group administered with vehicle PBS, and B represents the group administered with plasminogen. The results showed that the fat deposition (indicated by arrow) in aortic sinus of mice in the group administered with plasminogen was remarkably less than that in the control group administered with vehicle PBS. It indicates that plasminogen can ameliorate fat deposition in aortic sinus.

The results showed that the fat deposition (indicated by arrow) in aortic sinus of mice in the group administered with plasminogen (FIG. 3B) was remarkably less than that in the control group administered with vehicle PBS (FIG. 3A). It indicates that plasminogen can ameliorate fat deposition in aortic sinus in atherosclerosis.

Example 4

Plasminogen Ameliorates Aortic Sinus Injury in ApoE Atherosclerosis Mice

Figure 4:
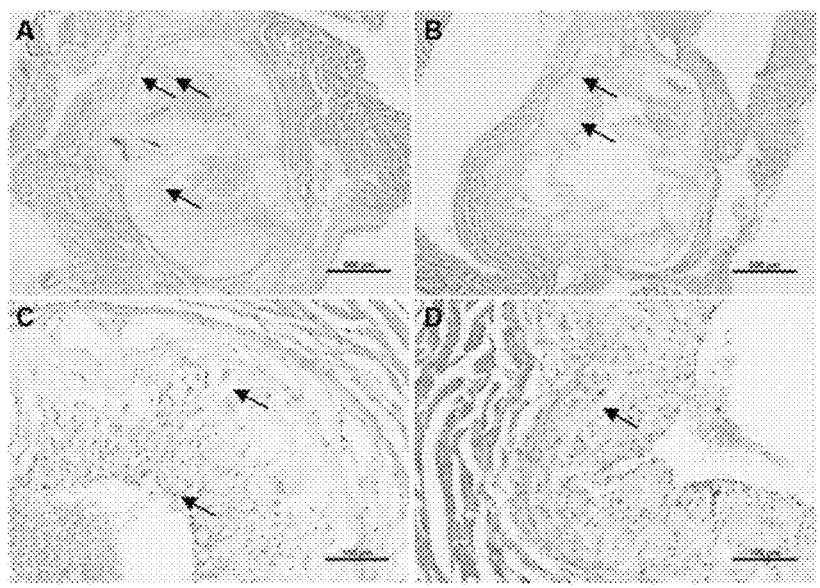
FIG. 4 shows a representative image of HE staining of aortic valve after administration of plasminogen to ApoE atherosclerosis model mice for 30 days. A and C refer to the control group administered with vehicle PBS, and B and D refer to the group administered with plasminogen. The results showed that the plaque deposition (indicated by arrow) in aortic valve of mice in the group administered with plasminogen (FIGS. 4B and 4D) was remarkably less than that in the control group administered with vehicle PBS (FIGS. 4A and 4C), and the degree of aortic valve fusion in the former group was less than that in the latter group. It indicates that plasminogen can ameliorate aortic valve injury in atherosclerosis model mice.

Thirteen 6-week-old male ApoE mice were fed with a high-fat and high-cholesterol diet (Nantong TROPHIC, TP2031) for 16 weeks to induce the hyperlipemia model [47,48]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The hearts were fixed in 4% paraformaldehyde for 24 to 48 hours. The fixed tissue samples were paraffin-embedded after dehydration with alcohol gradient and permeabilization with xylene. The aortic sinus tissue sections were 3 μm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 40× (FIGS. 4A and 4B) and 200× (FIGS. 4C and 4D), respectively.

The staining results showed that the lipid plaque deposition (indicated by arrow) in aortic sinus of mice in the group administered with plasminogen (FIGS. 4B and 4D) was remarkably less than that in the control group administered with vehicle PBS (FIGS. 4A and 4C), and the degree of aortic valve fusion in the former group was less than that in the latter group. It indicates that plasminogen can ameliorate aortic valve injury in atherosclerosis.

Example 5

Plasminogen Reduces Lipid Deposition in aorta of ApoE Atherosclerosis Mice

Thirteen 6-week-old male ApoE mice were fed with a high-fat and high-cholesterol diet (Nantong TROPHIC, TP2031) for 16 weeks to induce the hyperlipemia model [47,48]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The aortas were fixed in 4% paraformaldehyde for 24 to 48 hours, then sedimented in 15% and 30% sucrose at 4° C. overnight, respectively, and embedded in OCT. The frozen sections were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 200×.

Figure 5:
FIG. 5 shows a representative image of oil red O staining of aorta after administration of plasminogen to ApoE atherosclerosis model mice for 30 days. A represents the control group administered with vehicle PBS, and B represents the group administered with plasminogen. The results showed that the area of oil red O staining of aorta (indicated by arrow) of mice in the group administered with plasminogen was remarkably less than that in the control group administered with vehicle PBS. It indicates that plasminogen can remarkably reduce lipid deposition in the aorta of atherosclerosis model mice, and ameliorate aortic inner wall injury.

The staining results showed that the area of deposition stained with oil red O in aorta (indicated by arrow) of mice in the group administered with plasminogen (FIG. 5B) was remarkably less than that in the control group administered with vehicle PBS (FIG. 5A). It indicates that plasminogen can remarkably reduce lipid deposition on the inner walls of blood vessels of aorta of ApoE atherosclerosis model mice, and ameliorate aortic injury.

Example 6

Plasminogen Elevates the High-Density Lipoprotein Cholesterol in Serum of Diabetic Mice Twenty 26-week-old male db/db mice were randomly divided into groups, 11 mice in the group administered with plasminogen, and 9 mice in the control group administered with vehicle PBS. Mice in the group administered with plasminogen were injected with human plasminogen at a dose of 2 mg/0.2 mL/mouse/day via the tail vein, and an equal volume of PBS was administered to mice in the control group administered with vehicle PBS via the tail vein. After continuous injection for 35 days, the whole blood was collected from removed eyeballs, and centrifuged at 3500 r/min at 4° C. for 10 min, and the supernatant was taken and detected for the high-density lipoprotein cholesterol (HDL-C). The high-density lipoprotein cholesterol was detected using a kit (Nanjing Jiancheng Bioengineering Institute, Cat# A112-1) according to the method of the kit.

Figure 6:
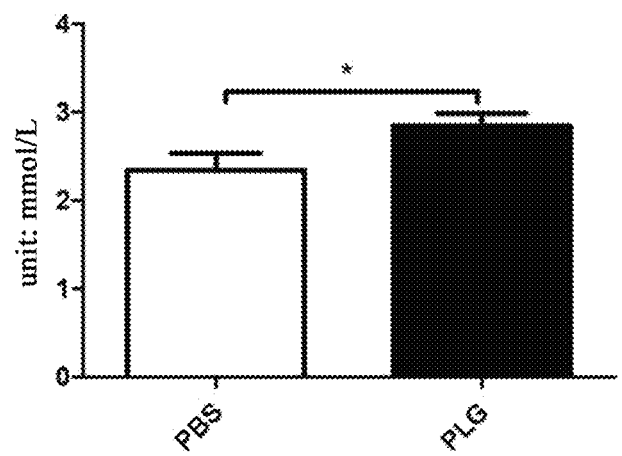
FIG. 6 shows detection results of the content of high-density lipoprotein cholesterol (HDL-C) in serum after administration of plasminogen to 26-week-old diabetic mice for 35 days. The results showed that after 35 days of injection of human plasminogen, the content of HDL-C in serum of mice in the group administered with plasminogen was significantly higher than that in the control group administered with vehicle PBS, and the statistical difference was significant (* indicates P<0.05). It indicates that injection of plasminogen can promote the increase in the content of HDL-C in serum.

The detection results showed that after continuous injection of human plasminogen into db/db mice for 35 days, the content of HDL-C in serum of mice in the group administered with plasminogen was higher than that in the control group administered with vehicle PBS (FIG. 6), and the statistical difference was significant.

Diabetes mellitus is usually complicated with cardiovascular atherosclerosis [45,46]. High-density lipoprotein is an anti-atherosclerosisplasma lipoprotein, a protective factor of coronary heart disease, commonly known as "vascular scavenger". The detection results demonstrate that plasminogen can elevate the level of serum HDL-C, and thus contribute to the improvement of atherosclerosis in diabetic mice.

Example 7

Plasminogen Lowers Low-Density Lipoprotein Cholesterol in Serum of Diabetic Mice Ten 24- to 25-week-old male db/db mice were randomly divided into groups, 5 mice in each of the group administered with plasminogen and the control group administered with vehicle PBS. Three db/m mice were taken as the normal control group. Mice in the group administered with plasminogen were injected with human plasminogen at a dose of 2 mg/0.2 mL/mouse/day via the tail vein, an equal volume of PBS was administered to mice in the PBS control group via the tail vein, and mice in the normal control group received no treatment. The first day of administration was set as Day 0. After continuous injection for 31 days, the whole blood was collected from removed eyeballs in mice, and centrifuged at 3500 r/min at 4° C. for 10 min, and the supernatant was taken and detected for the low-density lipoprotein cholesterol (LDL-C). The low-density lipoprotein cholesterol was detected using a kit (Nanjing Jiancheng Bioengineering Institute, Cat# A113-1) according to the method of the kit.

Figure 7:
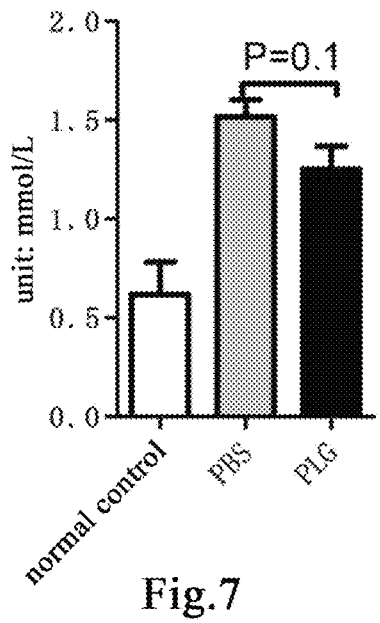
FIG. 7 shows detection results of the content of low-density lipoprotein cholesterol (LDL-C) in serum after administration of plasminogen to 24- to 25-week-old diabetic mice for 31 days. The results showed that after continuous injection of human plasminogen into diabetic model mice for 31 days, the content of LDL-C in serum of mice in the group administered with plasminogen was lower than that in the control group administered with vehicle PBS. It indicates that plasminogen can lower the content of LDL-C in serum.

The detection results showed that after continuous injection of human plasminogen into db/db mice for 31 days, the content of LDL-C in serum of mice in the group administered with plasminogen was lower than that in the control group administered with vehicle PBS (FIG. 7).

Low-density lipoprotein is a lipoprotein particle that carries cholesterol into peripheral tissue cells and can be oxidized into oxidized low-density lipoprotein. When low-density lipoprotein, particularly oxidized low-density lipoprotein (OX-LDL) is in excess, the cholesterol it carries accumulates on the arterial wall, causing arteriosclerosis. Therefore, low-density lipoprotein cholesterol is called "bad cholesterol" [52]. The experiment results demonstrate that plasminogen can reduce the content of low-density lipoprotein cholesterol in serum, and thus contribute to the control of atherosclerosis.

Example 8

Effect of Plasminogen on Body Weight of ApoE Atherosclerosis Mice

Thirteen 6-week-old male ApoE mice were fed with a high-fat and high-cholesterol diet (Nantong TROPHIC, TP2031) for 16 weeks to induce the hyperlipemia model [47,48]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 30 days. During the administration, mice continued to be fed with a high-fat and high-cholesterol diet. Mice were weighed on Day 1 and Day 31 of administration.

Figure 8:
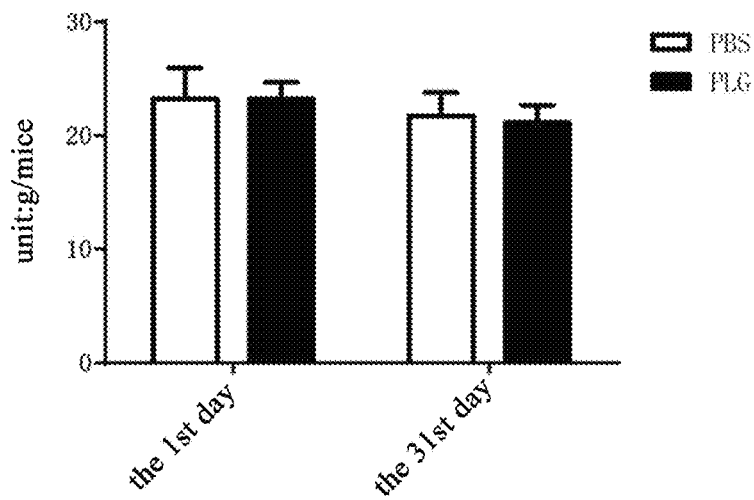
FIG. 8 shows changes in body weight after administration of plasminogen to ApoE atherosclerosis model mice for 30 days. The results showed that there was no remarkable change in body weight of mice after administration of plasminogen for 30 days, indicating that administration had no remarkable effect on the body weight of the ApoE atherosclerosis model mice.

The results showed that there was no significant change in body weight of mice after administration of plasminogen for 30 days (FIG. 8), indicating that administration had no remarkable effect on the body weight of the ApoE atherosclerosis model mice.

Example 9

Plasminogen Lowers the Content of Blood Lipid in ApoE Atherosclerosis Mice

Thirteen 6-week-old male ApoE mice were fed with a high-fat and high-cholesterol diet (Nantong TROPHIC, TP2031) for 16 weeks to induce the hyperlipemia model [47,48]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. On Day 30, the mice fasted for 16 hours, and on Day 31, the blood was collected from removed eyeballs, and centrifuged to obtained a supernatant, which was used in detecting the content of serum total cholesterol (T-CHO), serum triglyceride (TG), and serum low-density lipoprotein cholesterol (LDL-C).

1. Content of Serum Total Cholesterol

The content of serum total cholesterol was detected using a detection kit (Nanjing Jiancheng Bioengineering Institute, Cat# A111-1) according to the method of the detection kit.

Figure 9:
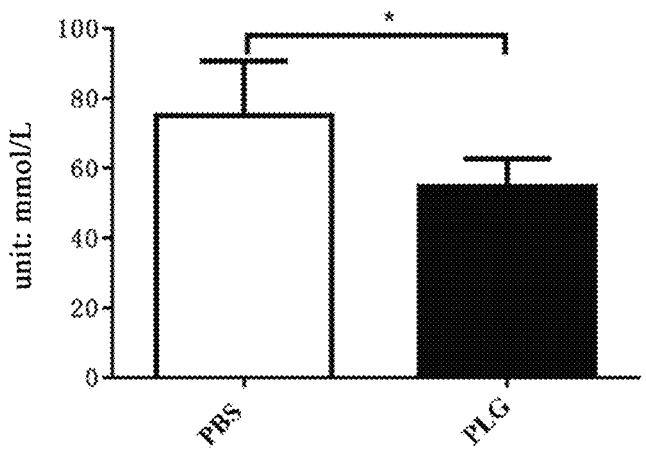
FIG. 9 shows detection results of serum total cholesterol after administration of plasminogen to ApoE atherosclerosis model mice for 30 days. The results showed that the concentration of total cholesterol in mice in the group administered with plasminogen was remarkably lower than that in the control group administered with vehicle PBS, and the statistical difference was significant (* indicates P<0.05). It indicates that plasminogen can lower the content of total cholesterol in serum of ApoE atherosclerosis model mice.

The detection results showed that the concentration of total cholesterol in mice in the group administered with plasminogen was remarkably lower than that in the control group administered with vehicle PBS, and the statistical difference was significant (FIG. 9). It indicates that plasminogen can lower the content of total cholesterol in serum of ApoE atherosclerosis model mice.

2. Content of Serum Triglyceride

Figure 10:
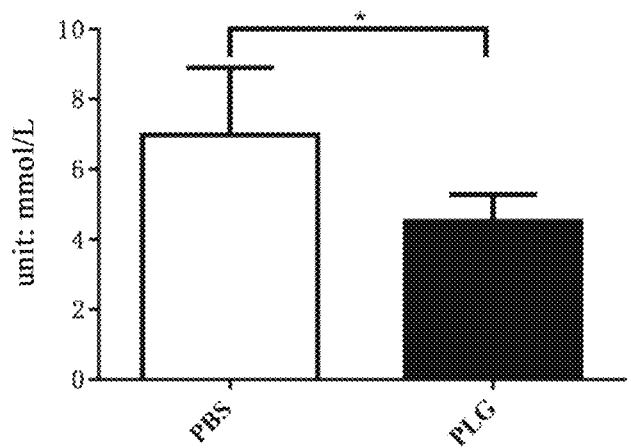
FIG. 10 shows detection results of serum triglyceride after administration of plasminogen to ApoE atherosclerosis model mice for 30 days. The results showed that the concentration of triglyceride in mice in the group administered with plasminogen was remarkably lower than that in the control group administered with vehicle PBS, and the statistical difference was significant (* indicates P<0.05). It indicates that plasminogen can lower the content of triglyceride in serum of ApoE atherosclerosis model mice.

The content of serum TG was detected using a TG detection kit (Nanjing Jiancheng Bioengineering Institute, Cat# A110-1) according to the COD-PAP method based on the instructions of the kit. The detection results showed that the concentration of TG in mice in the group administered with plasminogen was remarkably lower than that in the control group administered with vehicle PBS, and the statistical difference was significant (FIG. 10).

3. Content of Serum Low-Density Lipoprotein Cholesterol

The content of serum low-density lipoprotein cholesterol was detected using a low-density lipoprotein cholesterol (LDL-C) detection kit (Nanjing Jiancheng Bioengineering Institute, Cat# A113-1) according to the method of the detection kit.

Figure 11:
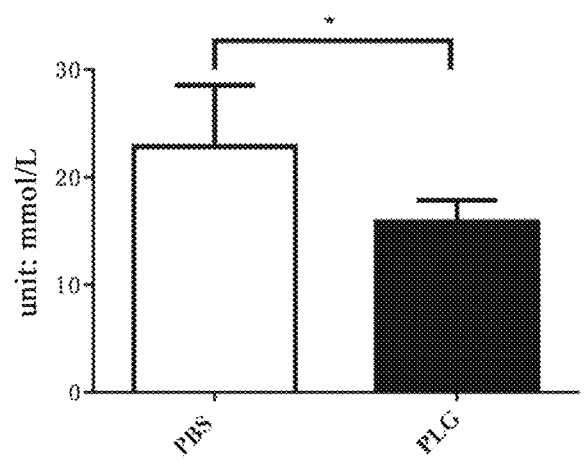
FIG. 11 shows detection results of serum low-density lipoprotein cholesterol (LDL-C) after administration of plasminogen to ApoE atherosclerosis model mice for 30 days. The results showed that the concentration of LDL-C in mice in the group administered with plasminogen was remarkably lower than that in the control group administered with vehicle PBS, and the statistical difference was significant (* indicates P<0.05). It indicates that plasminogen can lower the content of LDL-C in serum of ApoE atherosclerosis model mice.

The detection results showed that the concentration of LDL-C in mice in the group administered with plasminogen was remarkably lower than that in the control group administered with vehicle PBS, and the statistical difference was significant (FIG. 11). It indicates that plasminogen can lower the content of LDL-C in serum of ApoE atherosclerosis model mice, and improve atherosclerosis.

The above-mentioned results demonstrate that plasminogen can remarkably lower the content of serum total cholesterol, triglyceride, and low-density lipoprotein cholesterol in atherosclerosis model mice, and improve atherosclerosis. Meanwhile, the risk of atherosclerotic complications, such as atherosclerotic cardiovascular disease, is reduced by lowering the content of serum total cholesterol, triglyceride, and low-density lipoprotein cholesterol.

Example 10

Plasminogen Ameliorates Compensatory Cardiac Hypertrophy in ApoE Atherosclerosis Mice Thirteen 6-week-old male ApoE mice were fed with a high-fat and high-cholesterol diet (Nantong TROPHIC, TP2031) for 16 weeks to induce the hyperlipemia model [47,48]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. After weighed on Day 31 of administration, the mice were sacrificed, their hearts were weighed, and cardiac coefficients were calculated. Cardiac coefficient (%)=heart weight/body weight× 100.

Figure 12:
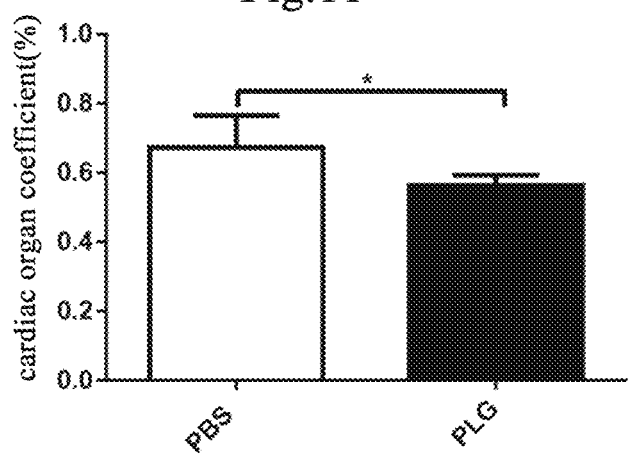
FIG. 12 shows statistical results of cardiac organ coefficient after administration of plasminogen to ApoE atherosclerosis model mice for 30 days. The results showed that the cardiac organ coefficient of mice in the group administered with plasminogen was remarkably lower than that in the control group administered with vehicle PBS. It indicates that plasminogen can ameliorate the compensatory cardiac hypertrophy caused by cardiac injury in ApoE atherosclerosis model mice.

The results showed that the cardiac coefficient of mice in the group administered with plasminogen was remarkably lower than that in the control group administered with vehicle PBS (FIG. 12). It indicates that plasminogen can alleviate the compensatory cardiac hypertrophy caused by cardiac injury in ApoE atherosclerosis model mice.

Example 11

Plasminogen Ameliorates Lipid Deposition in Liver of ApoE Atherosclerosis Mice

Thirteen 6-week-old male ApoE mice were fed with a high-fat and high-cholesterol diet (Nantong TROPHIC, TP2031) for 16 weeks to induce the hyperlipemia model [47,48]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The livers were fixed in 4% paraformaldehyde for 24 to 48 hours, then sedimented in 15% and 30% sucrose at 4° C. overnight, respectively, and embedded in OCT. The frozen sections were 8 μm thick, stained with oil red O for 15 min, differentiated with 75% ethanol for 5 s, followed by nuclear staining with hematoxylin for 30 s, and sealing with glycerine and gelatin. The sections were observed under an optical microscope at 400×.

Figure 13:
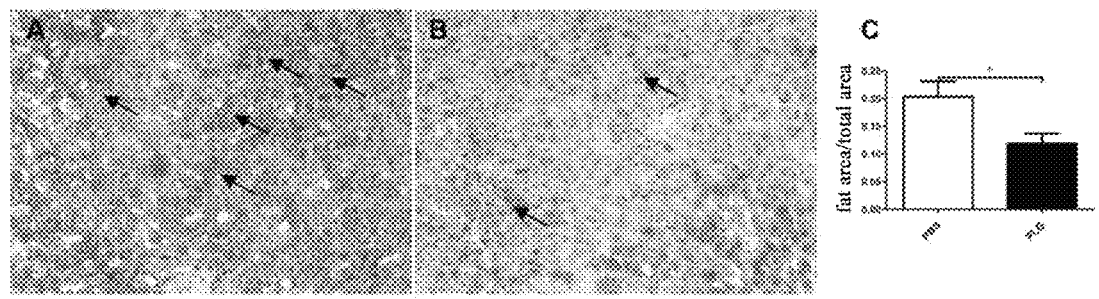
FIG. 13 shows a representative image of oil red O staining of liver after administration of plasminogen to ApoE atherosclerosis model mice for 30 days. A represents the control group administered with vehicle PBS, B represents the group administered with plasminogen, and C represents the quantitative analysis results. The results showed that the fat deposition (indicated by arrow) in liver of mice in the group administered with plasminogen was remarkably less than that in the control group administered with vehicle PBS, and the statistical difference was significant (* indicates P<0.05). It indicates that plasminogen can ameliorate fat deposition in liver of atherosclerosis model mice.

The staining results showed that the fat deposition (indicated by arrow) in liver of mice in the group administered with plasminogen (FIG. 13B) was remarkably lower than that in the control group administered with vehicle PBS (FIG. 13A), and the quantitative analysis showed significant statistical difference (FIG. 13C). It indicates that plasminogen can ameliorate fat deposition in liver of ApoE atherosclerosis model mice.

Example 12

Plasminogen Ameliorates Cardiac Injury in ApoE Atherosclerosis Mice

Figure 14:
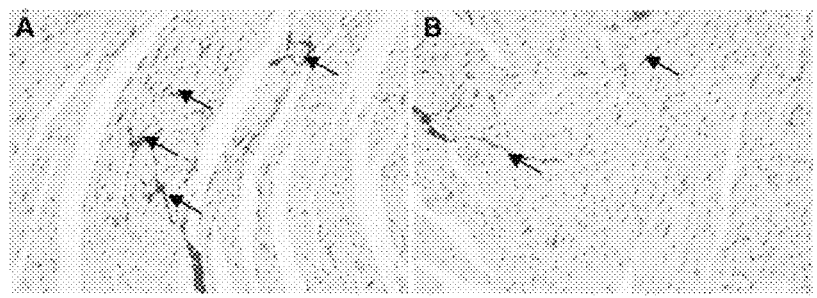
FIG. 14 shows a representative image of IgM immunostaining of heart after administration of plasminogen to ApoE atherosclerosis model mice for 30 days. A represents the control group administered with vehicle PBS, and B represents the group administered with plasminogen. The results showed that the positive expression of IgM (indicated by arrow) in the heart of mice in the group administered with plasminogen was remarkably less than that in the control group administered with vehicle PBS, indicating that plasminogen can promote the repair of cardiac injury caused by atherosclerosis.

Thirteen 6-week-old male ApoE mice were fed with a high-fat and high-cholesterol diet (Nantong TROPHIC, TP2031) for 16 weeks to induce the hyperlipemia model [47,48]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The hearts were fixed in 4% paraformaldehyde for 24 to 48 hours. The fixed tissues were paraffin-embedded after dehydration with alcohol gradient and permeabilization with xylene. The thickness of the tissue sections was 3 μm. The sections were dewaxed and rehydrated and washed with water once. The tissues were circled with a PAP pen, incubated with 3% hydrogen peroxide for 15 minutes, and washed with 0.01M PBS twice for 5 minutes each time. The sections were blocked with 5% normal goat serum (Vector laboratories, Inc., USA) for 30 minutes, and after the time was up, the goat serum liquid was discarded. Goat anti-mouse IgM (HRP) antibody (Abcam) was added to the sections dropwise, incubated for 1 hour at room temperature and washed with 0.01M PBS twice for 5 minutes each time. The sections were developed with a DAB kit (Vector laboratories, Inc., USA). After washed with water, the sections were counterstained with hematoxylin for 30 seconds and flushed with running water for 5 minutes. After dehydration with alcohol gradient, permeabilization with xylenehe, and sealing with a neutral gum, the sections were observed under an optical microscope at 200×. IgM antibodies play an important role during the clearance of apoptotic and necrotic cells, and the local level of IgM antibodies at the injury site in tissues and organs are positively correlated with the degree of injury [50,51]. Therefore, detection of local level of IgM antibodies in tissues and organs can reflect the injury of the tissues and organs. The experiment showed that the positive expression of IgM in the heart of mice in the group administered with plasminogen (FIG. 14B) was remarkably less than that in the control group administered with vehicle PBS (FIG. 14A). It indicates that plasminogen can remarkably ameliorate myocardial injury in ApoE mice.

Example 13

Plasminogen Lowers the Level of Cardiac Fibrosis in ApoE Atherosclerosis Mice

Thirteen 6-week-old male ApoE mice were fed with a high-fat and high-cholesterol diet (Nantong TROPHIC, TP2031) for 16 weeks to induce the hyperlipemia model [47,48]. 50 μL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The administration lasted for 30 days. During the administration, mice continued to be fed with a high-fat and high-cholesterol diet. The mice were sacrificed on Day 31. The hearts were fixed in 4% paraformaldehyde for 24 to 48 hours. The fixed tissues were paraffin-embedded after dehydration with alcohol gradient and permeabilization with xylene. The tissue sections was 3 µm thick. The sections were dewaxed and rehydrated and washed with water once. After stained with 0.1% Sirius red in saturated picric acid for 30 min, the sections were flushed with running water for 2 min After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 200×.

Sirius red staining allows for long-lasting staining of collagen, and is a special staining method for collagen tissue in pathological sections to show collagen tissue specifically.

Figure 15:
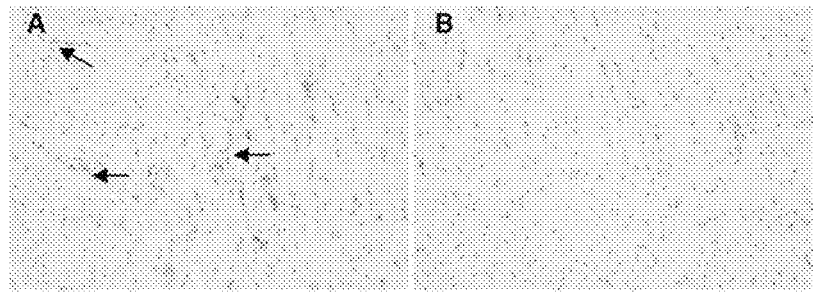
FIG. 15 shows a representative image of Sirius red staining of heart after administration of plasminogen to ApoE atherosclerosis model mice for 30 days. A represents the control group administered with vehicle PBS, and B represents the group administered with plasminogen. The results showed that the collagen deposition (indicated by arrow) in the group administered with plasminogen was remarkably less than that in the control group administered with vehicle PBS, indicating that plasminogen can alleviate cardiac fibrosis in ApoE atherosclerosis model mice.

The staining results showed that the collagen deposition (indicated by arrow) in the group administered with plasminogen (FIG. 15B) was remarkably less than that in the control group administered with vehicle PBS (FIG. 15A), indicating that plasminogen can lower collagen deposition in cardiac tissue and reduce cardiac fibrosis in ApoE atherosclerosis model mice.

Example 14

Plasminogen Lowers Lipid Deposition in Ventricle of Diabetic Mice

Diabetes mellitus is usually complicated with cardiovascular atherosclerosis [45,46]. Cardiovascular atherosclerosis can lead to ischemic injury of cardiac myocytes. Oil red O staining can show lipid deposition and reflect the severity of injury [49].

Nine 26-week-old male db/db mice were randomly divided into two groups, 4 mice in the group administered with plasminogen, and 5 mice in the control group administered with vehicle PBS. Mice in the group administered with plasminogen were injected with human plasminogen at a dose of 2 mg/0.2 mL/mouse/day via the tail vein, and an equal volume of PBS was administered to mice in the control group administered with vehicle PBS via the tail vein, both lasting for 35 days. The mice were sacrificed on Day 36. The hearts were fixed in 4% paraformaldehyde for 24 to 48 hours, then sedimented in 15% and 30% sucrose at 4° C. overnight, respectively, and embedded in OCT. The frozen sections were 8 µm thick, stained with oil red O for 15 min, differentiated with 75% ethanol for 5 s, followed by nuclear staining with hematoxylin for 30 s, and sealing with glycerine and gelatin. The sections were observed under an optical microscope at 400×.

Figure 16:
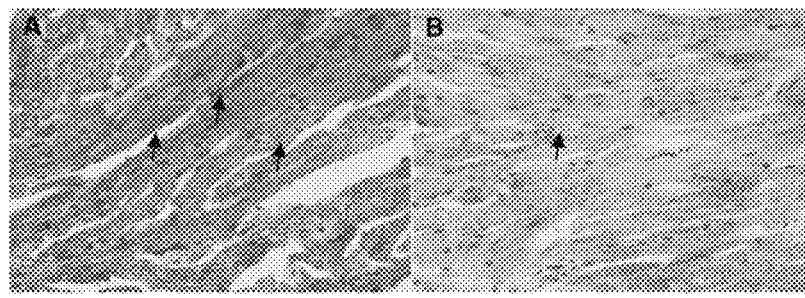
FIG. 16 shows a representative image of oil red O staining of ventricle after administration of plasminogen to 26-week-old diabetic mice for 35 days. A represents the control group administered with vehicle PBS, and B represents the group administered with plasminogen. The results showed that the lipid deposition in ventricle (indicated by arrow) of mice in the group administered with plasminogen was remarkably less than that in the control group administered with vehicle PBS. It indicates that plasminogen can reduce lipid deposition in ventricle of diabetic mice, and promote the repair of ventricular injury.

The results showed that the lipid deposition (indicated by arrow) in ventricle of mice in the group administered with plasminogen (FIG. 16B) was remarkably less than that in the control group administered with vehicle PBS (FIG. 16A). It indicates that plasminogen can reduce lipid deposition in ventricle of diabetic mice, and promote the repair of ventricular injury.

Example 15

Plasminogen Ameliorates Aortic Sinus Fibrosis in ApoE Atherosclerosis Mice

Figure 17:
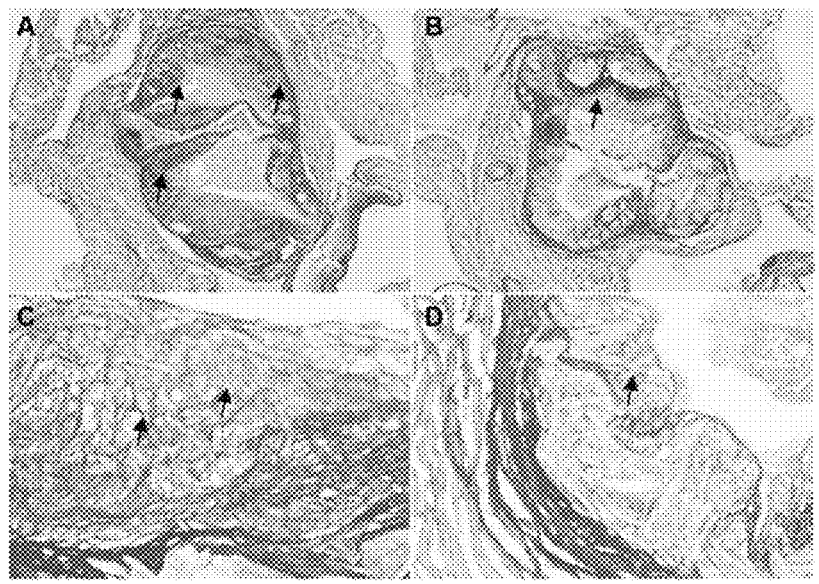
FIG. 17 shows a representative image of Sirius red staining of aortic sinus after administration of plasminogen to ApoE atherosclerosis model mice for 30 days. A and C refer to the control group administered with vehicle PBS, and B and D refer to the group administered with plasminogen. The results showed that the area of collagen deposition (indicated by arrow) on the inner walls of blood vessels of aortic sinus in the group administered with plasminogen was remarkably less than that in the control group administered with vehicle PBS, indicating that plasminogen can alleviate the fibrosis level of aortic sinus of arteriosclerosis model mice.

Thirteen 6-week-old male ApoE mice were fed with a high-fat and high-cholesterol diet (Nantong TROPHIC, TP2031) for 16 weeks to induce the atherosclerosis model [31,32]. 50 µL of blood was taken from each model mouse three days before administration, and the total cholesterol (T-CHO) content was detected. The mice were randomly divided into two groups based on the T-CHO content, 7 mice in the control group administered with vehicle PBS, and 6 mice in the group administered with plasminogen. The first day of administration was set as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. The mice were administered for 30 days and sacrificed on Day 31. The hearts were fixed in 4% paraformaldehyde for 24 to 48 hours, then sedimented in 15% and 30% sucrose at 4° C. overnight, respectively, and embedded in OCT. The frozen sections were 8 µm thick. After stained with 0.1% Sirius red in saturated picric acid for 30 min, the sections were flushed with running water for 2 min After stained with hematoxylin for 1 min, the sections were flushed with running water, differentiated with 1% hydrochloric acid in alcohol, returned to blue with ammonia water, flushed with running water, dried and sealed with a neutral gum. The sections were observed under an optical microscope at 40×. FIGS. 17C and D are enlarged images of the black-framed areas of FIGS. 17A and B respectively.

The results showed that the area of collagen deposition (indicated by arrow) in the group administered with plasminogen (FIGS. 17B and 17D) was remarkably less than that in the control group administered with vehicle PBS (FIGS. 17A and 17C), indicating that plasminogen can reduce the level of aortic sinus fibrosis in arteriosclerosis model mice.

Example 16

Protective Effect of Plasminogen on the Aortic Inner Wall Injury in Diabetic Mice Ten 24- to 25-week-old male db/db mice were weighed on the day the experiment started, i.e. Day 0, and were randomly divided into two groups based on the body weight, 5 mice in each of the control group administered with vehicle PBS and the group administered with plasminogen. Plasminogen or PBS (PBS refers to Phosphate Buffer Saline, as the vehicle of plasminogen herein) was administered from Day 1 for 31 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS in the same manner. Mice were sacrificed on Day 32, and the aortas were fixed in 10% neutral formalin fixative for 24 hours. The fixed tissue samples were paraffin-embedded after dehydration with alcohol gradient and permeabilization with xylene. The tissue sections were 5 µm thick. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient, and observed under an optical microscope at 400×.

Figure 18:
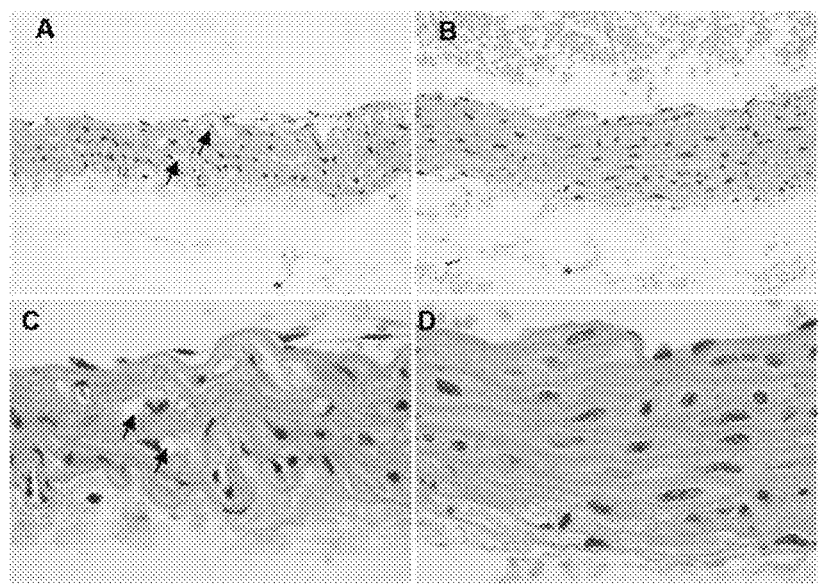
FIG. 18 shows an image of HE staining of aorta after administration of plasminogen to 24- to 25-week-old diabetic mice for 31 days. A represents the control group administered with vehicle PBS, and B represents the group administered with plasminogen. The results showed that in the control group administered with vehicle PBS, there was a foam cell deposition (indicated by arrow) on the vascular wall, the middle elastic membrane was arranged in disorder, and the vascular wall was accidented; while in the group administered with plasminogen, the middle elastic membrane had a regular structure in a wave shape. It indicates that the injection of plasminogen has a certain repair effect on aortic injury caused by diabetes mellitus.

The HE staining results showed that in the control group administered with vehicle PBS, there was a foam cell deposition (indicated by arrow) on the vascular wall, the middle elastic membrane was arranged in disorder, and the vascular wall was accidented (FIG. 18A); while in the group administered with plasminogen, the middle elastic membrane had a regular structure in a wave shape (FIG. 18B). It indicates that the injection of plasminogen has a certain repair effect on aortic inner wall injury caused by diabetes mellitus.

Example 17

Protective Effect of Plasminogen on the Myocardial Injury in Diabetic Mice

Diabetes mellitus is usually complicated with cardiovascular atherosclerosis [45,46]. Cardiovascular atherosclerosis can lead to ischemic injury of cardiac myocytes. Cardiac troponin I (CTNI) is an important marker of myocardial injury, and its serum concentration can reflect the extent of myocardial injury [44]. In this experiment, the repair effect of plasminogen on myocardial injury was observed by detecting cardiac troponin I.

Figure 19:
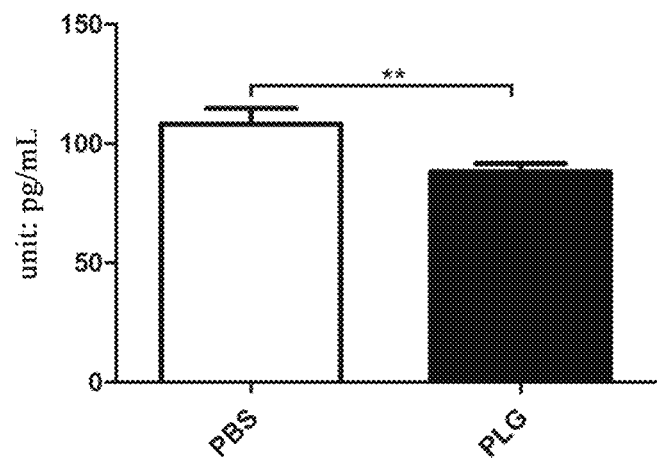
FIG. 19 shows detection results of the content of troponin in serum after administration of plasminogen to 24- to 25-week-old diabetic mice for 31 days. The results showed that the concentration of cardiac troponin I in the group administered with plasminogen was remarkably lower than that in the control group administered with vehicle PBS, and the statistical difference was extremely significant (** indicates P<0.01). It indicates that plasminogen can remarkably promote the repair of myocardial injury in mice with late-stage diabetes mellitus.

Twenty-eight 24- to 25-week-old male db/db mice were weighed on the day the experiment started, i.e. Day 0, and were randomly divided into two groups based on the body weight, 12 mice in the control group administered with vehicle PBS, and 16 mice in the group administered with plasminogen. From the second day after grouping, i.e. Day 1, plasminogen or PBS was administered for 31 consecutive days. Mice in the group administered with plasminogen were injected with plasminogen at a dose of 2 mg/0.2 mL/mouse/day via the tail vein, and an equal volume of PBS was administered to mice in the control group administered with vehicle PBS via the tail vein. On day 32, blood was taken from the removed eyeballs and centrifuged at 3500 r/min for 15-20 minutes, and the supernatant was used for detection for determining cardiac troponin I concentration. The results showed that the concentration of cardiac troponin I in the group administered with plasminogen was remarkably lower than that in the control group administered with vehicle PBS, and the statistical difference was extremely significant (FIG. 19). It indicates that plasminogen can remarkably promote the repair of myocardial injury caused by cardiovascular atherosclerosis in diabetic mice.

Example 18

Plasminogen Increases the Concentration of Serum High-Density Lipoprotein Cholesterol in 3% Cholesterol Hyperlipemia Model Mice Sixteen 9-week-old male C57 mice were fed with a 3% cholesterol high-fat diet (Nantong TROPHIC) for 4 weeks to induce hyperlipemia [52,53]. This model was designated as the 3% cholesterol hyperlipemia model. The model mice continued to be fed with a 3% cholesterol high-fat diet. 50 µL of blood was taken from each mouse three days before administration, and the total cholesterol was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein, both lasting for 20 days. On Day 10 and Day 20, the mice fasted for 16 hours, and on Day 11 and Day 21, 50 µL of blood was collected from orbital venous plexus, and centrifuged to obtain a supernatant, which was used in detecting the serum high-density lipoprotein cholesterol (HDL-C). The content of high-density lipoprotein cholesterol herein was detected by the method as described in a detection kit (Nanjing Jiancheng Bioengineering Institute, Cat# A112-1).

Figure 20:
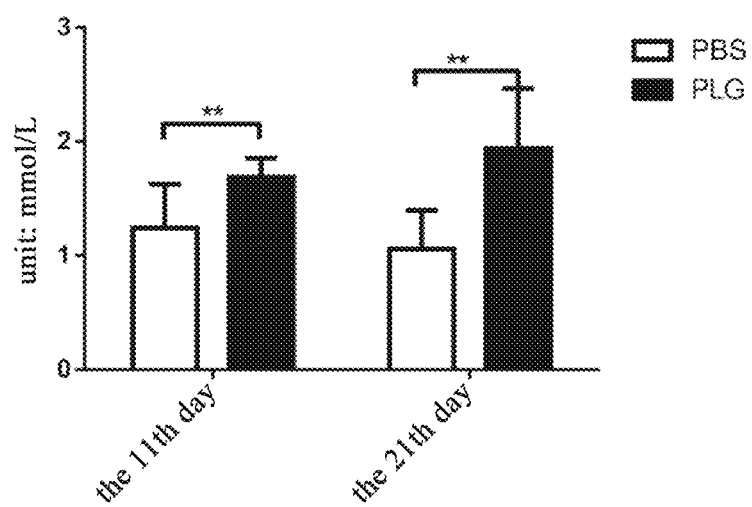
FIG. 20 shows detection results of serum high-density lipoprotein cholesterol after administration of plasminogen to 3% cholesterol hyperlipemia model mice for 10 days and 20 days. The results showed that the concentration of HDL-C in serum of mice in the group administered with plasminogen was remarkably higher than that in the control group administered with vehicle PBS, and the high-density lipoprotein concentrations of the two groups were statistically different after administration for 10 or 20 days (** indicates P<0.01). It indicates that plasminogen can effectively elevate the content of high-density lipoprotein cholesterol in serum of hyperlipemia model mice, and improve the dyslipidemia in hyperlipemia model mice.

The detection results showed that the concentration of HDL-C in serum of mice in the group administered with plasminogen was remarkably higher than that in the control group administered with vehicle PBS, and the HDL-C concentrations of the two groups were statistically different after administration for 10 or 20 days (FIG. 20). It indicates that plasminogen can elevate the content of high-density lipoprotein cholesterol in serum of hyperlipemia model mice, and improve the dyslipidemia in mice with hyperlipemia.

Example 19

Plasminogen Lowers Risk of Atherosclerosis Formation in 3% Cholesterol Hyperlipemia Model Mice Sixteen 9-week-old male C57 mice were fed with a 3% cholesterol high-fat diet (Nantong TROPHIC) for 4 weeks to induce hyperlipemia [52,53]. This model was designated as the 3% cholesterol hyperlipemia model. The model mice continued to be fed with a 3% cholesterol high-fat diet. 50 µL of blood was taken from each mouse three days before administration, and the total cholesterol (T-CHO) was detected. The mice were randomly divided into two groups based on the total cholesterol concentration and the body weight, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. After administration on Day 20, the mice began to fast for 16 hours, and on Day 21, 50 µL of blood was collected from orbital venous plexus, and centrifuged to obtain a supernatant. The total cholesterol content was detected by using a total cholesterol detection kit (Nanjing Jiancheng Bioengineering Institute, Cat# A111-1); and the high-density lipoprotein cholesterol (HDL-C) content was detected using a high-density lipoprotein cholesterol detection kit (Nanjing Jiancheng Bioengineering Institute, Cat# A112-1).

Atherosclerosis index is a comprehensive index to predict atherosclerosis clinically. It is considered to be of greater clinical importance as an estimate of the risk of coronary heart disease than total cholesterol, triglyceride, high-density lipoprotein, and low-density lipoprotein alone [54]. Atherosclerosis index=(T-CHO-HDL-C)/HDL-C.

Figure 21:
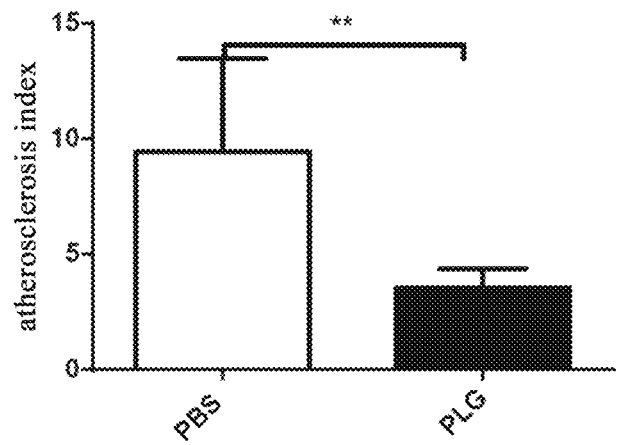
FIG. 21 shows calculation results of atherosclerosis index after administration of plasminogen to 3% cholesterol hyperlipemia model mice for 20 days. The calculation results showed that the atherosclerosis index of mice in the group administered with plasminogen was remarkably lower than that in the control group administered with vehicle PBS, and the statistical difference was significant. It indicates that plasminogen can lower the risk of atherosclerosis in hyperlipemia model mice.

The calculation results showed that the atherosclerosis index of mice in the group administered with plasminogen was remarkably lower than that in the control group administered with vehicle PBS, and the statistical difference was significant (FIG. 21). It indicates that plasminogen can lower the risk of atherosclerosis in hyperlipemia model mice.

Example 20

Plasminogen Lowers Risk of Onset of Heart Disease in 3% Cholesterol Hyperlipemia Model Mice Sixteen 9-week-old male C57 mice were fed with a 3% cholesterol high-fat diet (Nantong TROPHIC) for 4 weeks to induce hyperlipemia [52,53]. This model was designated as the 3% cholesterol hyperlipemia model. The model mice continued to be fed with a 3% cholesterol high-fat diet. 50 µL of blood was taken from each mouse three days before administration, and the total cholesterol (T-CHO) was detected. The mice were randomly divided into two groups based on the total cholesterol concentration, 8 mice in each group. The first day of administration was recorded as Day 1. Mice in the group administered with plasminogen were injected with human plasminogen at a dose of 1 mg/0.1 mL/mouse/day via the tail vein, and an equal volume of PBS was administered to mice in the control group administered with vehicle PBS via the tail vein. After administration on Day 20, the mice began to fast for 16 hours, and on Day 21, 50 µL of blood was collected from orbital venous plexus, and centrifuged to obtain a supernatant. The total cholesterol content was detected by using a total cholesterol detection kit (Nanjing Jiancheng Bioengineering Institute, Cat# A111-1); and the high-density lipoprotein cholesterol (HDL-C) content was detected using a high-density lipoprotein cholesterol detection kit (Nanjing Jiancheng Bioengineering Institute, Cat# A112-1). Cardiac risk index=T-CHO/HDL.

Cardiac risk index (CRI) is used to assess the risk of heart disease induced by dyslipidemia[54].

Figure 22:
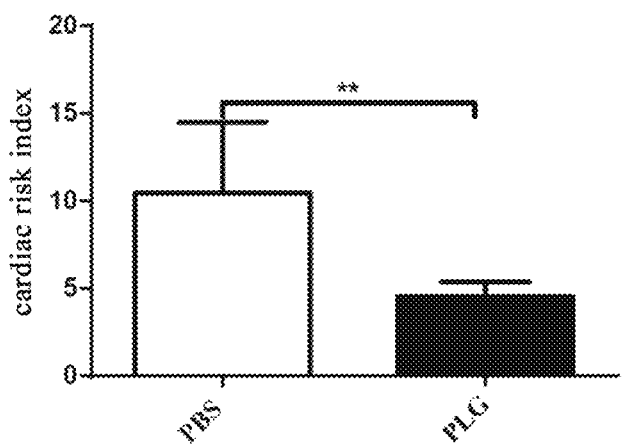
FIG. 22 shows calculation results of cardiac risk index after administration of plasminogen to 3% cholesterol hyperlipemia model mice for 20 days. The results showed that CRI in the group administered with plasminogen was remarkably lower than that in the control group administered with vehicle PBS, and the statistical difference was extremely significant. It indicates that plasminogen can effectively lower the risk of heart disease in hyperlipemia model mice.

The results showed that CRI in the group administered with plasminogen was remarkably lower than that in the control group administered with vehicle PBS, and the statistical difference was extremely significant (FIG. 22). It indicates that plasminogen can effectively lower the risk of heart disease in hyperlipemia model mice.

References

[1] Libby, Ridker P M, Maseri A. Inflammation in atherosclerosis [J]. Circulation, 2002, 105(9):1135-1143.

[2] Esper R J, Vilarino J O, Machado R A, et al. Endothelial dysfunction in normal and abnormal glucosemetabolism [J]. Adv Cardiol, 2008, 45:17-43.

[3] Boos C J, Blann A D, Lip G Y. Assessment of endothelial damage/dysfunction: A focus on circulating endothelial cells [J]. Methods Mol Med, 2007, 139:211-224.

[4] Ott S J, El Mokhtari N E, Musfeldt M, et al. Detection of diverse bacterial signatures in atheroscleroticlesions of patients with coronary heart disease [J]. Circulation, 2006, 113 (7): 929-937.

[5] Ellahham S. Role of antiplatelet agents in the primary and secondary prevention of atherothrombotic events in high risk-patients [J]. South Med J, 2008, 101(3):273-283.

[6] Kanani P M, Sperling M A. Hyperlipidemia in adolescents[J]. Adolesc Med, 2002, 13(1):37-52.

[7] Eo H S, Kim D I. Apolipoprotein C1 and apolipoprotein E are differentially expressed in atheroma of the carotid and femoral artery [J]. J Surg Res, 2008, 144 (1):132-137.

[8] Hansson G K, Libby P, Schonbeck U, et al. Innate and adaptive immunity in the pathogenesis of atherosclerosis [J]. Circ Res, 2002, 91(4):281-291.

[9] Boyle J J. Macrophage activation in atherosclerosis: Pathogenesis and pharmacology of plaque rupture [J]. CurrVascPharmacol, 2005, 3(1):63-68.

[10] Jia G, Cheng G, grawal D K. Differential effects of insulin-like growth factor-1 and atheroma-associated cytokines on cell proliferation and apoptosis in plaque smooth muscle cells of symptomatic and asymptomatic patients with carotidstenosis [J]. Immunol Cell Biol, 2006, 84(5):422-429.

[11] Clarke M, Bennett M. The emerging role of vascular smooth muscle cell apoptosis in atherosclerosis and plaques tability [J]. Am J Nephrol, 2006, 26(6):531-535.

[12] Wen ting et al., Study on the mechanism of diabetes mellitus combined with atherosclerosis. Chin J Clinicians (Electronic Edition), April 1, 2016, Vol. 10, No. 7.

[13] Lopez-Pedera C, Aguirre M A. Accelerated atherosclerosis in systemic lupus erythematosus: role of proinflammatory cytokines and therapeutic approaches [J]. J Biomed Biotechnol, 2010, 2010:

[14] Gong Z, Xing S, Zheng F, et al. Increased expression of macrophage migration inhibitory factor in aorta of patients with coronary atherosclerosis [J]. J Cardiovasc Surg (Torino), 2015, 56(4): 631-637.

[15] Kim J, Kim K M, Kim C S, et al. Puerarin inhibits the retinal pericyte apoptosis induced by advanced glycation end products in vitro and in vivo by inhibiting NADPH oxidase-related oxidative stress [J]. Free RadicBiol Med, 2012, 53(2): 357-365.

[16] Koulis C, Kanellakis P. Role of bone-marrow and non-bone marrow-drived receptor for advanced glycation end-products (RAGE) in a mouse model of diabetes-associated atherosclerosis [J]. Clin Sci (Lond), 2014, 127(7): 485-497.

[17] Tsukano H, Gotoh T, Endo M, et al. The endoplasmic reticulum stress-C/EBP homologous protein pathway-mediated apoptosis in macrophages contributes to the instability of atherosclerotic plaques [J]. ArteriosclerThrombVascBiol, 2010, 30(10): 1925-1932.

[18] Martínez-Hervás S, Vinué A, Núñez L, et al. Insulin resistance aggravates atherosclerosis by reducing vascular smooth muscle cell survival and increasing CX3CL1/CX3CR1 axis [J]. Cardiovasc Res, 2014, 103(2): 324-336.

[19] Oh J, Riek A E, Darwech I, et al. Deletion of macrophage Vitamin D receptor promotes insulin resistance and monocyte cholesterol transport to accelerate atherosclerosis in mice [J]. Cell Rep, 2015, 10(11): 187218-187286.

[20] Marfella R, D' Amico M, Di Filippo C, et al. The possible role of the ubiquitin proteasome system in the development of atherosclerosis in diabetes [J]. Cardiovasc Diabetol, 2007, 6: 35.

[21] Lassila M, Allen T J, Cao Z, et al. Imatinib attenuates diabetes associated atherosclerosis [J]. ArteriosclerThrombVascBiol, 2004, 24(5): 935-942.

[22] He C, Medley S C, Hu T, et al. PDGFRβ signalling regulates local inflammation and synergizes with hypercholesterolaemia to promote atherosclerosis [J]. Nat Commun, 2015, 6: 7770.

[23] Alexander C M and Werb, Z. (1991). Extracellular matrix degradation. In Cell Biology of Extracellular Matrix, Hay ED, ed. (New York: Plenum Press), pp. 255-302.

[24] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.

[25] He, C. S., Wilhelm, S. M., Pentland, A. P., Marmer, B. L., Grant, G. A., Eisen, A. Z., and Goldberg, G. I. (1989).

Tissue cooperation in a proteolytic cascade activating human interstitial collagenase. Proc. Natl. Acad. Sci. U.S.A 86, 2632-2636.

[26] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U. S. A 82, 4939-4943.

[27] Vassalli, J. D., Baccino, D., and Belin, D. (1985). A cellular binding site for the Mr 55,000 form of the human plasminogen activator, urokinase. J. Cell Biol. 100, 86-92.

[28] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[29] Saksela, O. and Rifkin, D. B. (1988). Cell-associated plasminogen activation: regulation and physiological functions. Annu. Rev. Cell Biol. 4, 93-126.

[30] Raum, D., Marcus, D., Alper, C. A., Levey, R., Taylor, P. D., and Starzl, T. E. (1980). Synthesis of human plasminogen by the liver. Science 208, 1036-1037.

[31] Wallén P (1980). Biochemistry of plasminogen. In Fibrinolysis, Kline D L and Reddy K K N, eds. (Florida: CRC).

[32] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U. S. A 72, 2577-2581.

[33] Collen, D. and Lijnen, H. R. (1991). Basic and clinical aspects of fibrinolysis and thrombolysis. Blood 78, 3114-3124.

[34] Alexander, C. M. and Werb, Z. (1989). Proteinases and extracellular matrix remodeling. Curr. Opin. Cell Biol. 1, 974-982.

[35] Mignatti, P. and Rifkin, D. B. (1993). Biology and biochemistry of proteinases in tumor invasion. Physiol Rev. 73, 161-195.

[36] Collen, D. (2001). Ham-Wasserman lecture: role of the plasminogen system in fibrin-homeostasis and tissue remodeling. Hematology. (Am. Soc. Hematol. Educ. Program.) 1-9.

[37] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[38] Andreasen, P. A., Kjoller, L., Christensen, L., and Duffy, M. J. (1997). The urokinase-type plasminogen activator system in cancer metastasis: a review. Int. J. Cancer 72, 1-22.

[39] Rifkin, D. B., Mazzieri, R., Munger, J. S., Noguera, I., and Sung, J. (1999). Proteolytic control of growth factor availability. APMIS 107, 80-85.

[40] Marder V J, Novokhatny V. Direct fibrinolytic agents: biochemical attributes, preclinical foundation and clinical potential [J]. Journal of Thrombosis and Haemostasis, 2010, 8(3): 433-444.

[41] Hunt J A, Petteway Jr S R, Scuderi P, et al. Simplified recombinant plasmin: production and functional comparison of a novel thrombolytic molecule with plasma-derived plasmin [J]. ThrombHaemost, 2008, 100(3): 413-419.

[42] Sottrup-Jensen L, Claeys H, Zajdel M, et al. The primary structure of human plasminogen: Isolation of two lysine-binding fragments and one "mini"-plasminogen (MW, 38,000) by elastase-catalyzed-specific limited proteolysis [J]. Progress in chemical fibrinolysis and thrombolysis, 1978, 3: 191-209.

[43] Nagai N, Demarsin E, Van Hoef B, et al. Recombinant human microplasmin: production and potential therapeutic properties [J]. Journal of Thrombosis and Haemostasis, 2003, 1(2): 307-313.

[44] R. Langhorn and J. L. Willesen. Cardiac Troponins in Dogs and Cats. J Vet Intern Med 2016; 30:36-50.

[45] Sun Mi Hwang,‡Jin Sook Kim, Yun Jung Lee et al. Anti-Diabetic Atherosclerosis Effect of Prunella vulgaris in db/db Mice with Type 2 Diabetes. The American Journal of Chinese Medicine, Vol. 40, No. 5, 937-951.

[46] Hardy, D. S., D. M. Hoelscher, C. Aragaki et al. Association of glycemic index and glycemic load with risk of incident coronary heart disease among Whites and African Americans with and without type 2 diabetes: the atherosclerosis risk in communities study. Ann. Epidemiol. 20: 610-616, 2010.

[47] Yutaka Nakashima, Andrew S. Plump, Elaine W. Raines et al. Arterioscler Thromb. 1994 Jan;14(1):133-40.

[48] Yvonne Nitschke, Gabriele Weissen-Plenz, Robert Terkeltaub et al. Npp 1 promotes atherosclerosis in ApoE knockout mice. J. Cell. Mol. Med. Vol 15, No 11, 2011 pp. 2273-2283.

[49] Siobhan M. Craige, PhD, Shashi Kant et al. Endothelial NADPH oxidase 4 protects ApoE−/− mice from atherosclerotic lesions. Free RadicBiol Med. 2015 December; 89: 1-7.

[50] Zhang M, Takahashi K, Alicot E M, Vorup-Jensen T, Kessler B, et al. (2006) Activation of the lectin pathway by natural IgM in a model of ischemia/reperfusion injury. J Immunol 177: 4727-4734.

[51] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement.

[52] Dominika Nackiewicz, Paromita Dey, Barbara Szczerba et al. Inhibitor of differentiation 3, a transcription factor regulates hyperlipidemia associated kidney disease. Nephron Exp Nephrol. 2014; 126(3): 141-147.

[53] Ming Gul, Yu Zhang., Shengjie Fan et al. Extracts of RhizomaPolygonatiOdorati Prevent High-Fat Diet-Induced Metabolic Disorders in C57BL/6 Mice. PLoS ONE 8(11): e81724.

[54] Sungwon Lee, Youngjoo Lee, Jiyeon Kim et al. Atorvastatin and rosuvastatin improve physiological parameters and alleviate immune dysfunction in metabolic disorders. BiochemBiophys Res Commun 2016 Sep 23; 478(3): 1242-7.

The invention claimed is:

1. A method for preventing and/or treating coronary atherosclerosis and its related conditions in a subject, comprising administering a prophylactically and/or therapeutically effective amount of plasminogen to the subject, wherein the subject suffers from, is suspected of suffering from coronary atherosclerosis and its related conditions, or has a risk of suffering from coronary atherosclerosis and its related conditions, and wherein plasminogen promotes serum level of the high-density lipoprotein cholesterol (HDL-C) in the subject.

2. The method of claim 1, wherein the coronary atherosclerosis-related conditions comprise coronary heart disease, angina pectoris, myocardial infarction, arrhythmia, and heart failure caused by coronary atherosclerosis.

3. The method of claim 1, wherein the coronary atherosclerosis is coronary atherosclerosis complicated with diabetes mellitus.

4. The method of claim 1, wherein the plasminogen prevents and/or treats coronary atherosclerosis in one or more ways selected from: lowering a serum total cholesterol level in the subject, lowering a serum triglyceride level in the subject, lowering a serum low-density lipoprotein level in the subject, elevating a serum high-density lipoprotein level in the subject, reducing lipid deposition on an arterial wall of the subject, promoting fat metabolism in the liver, promoting fat transport in the liver, and reducing fat deposition in the liver of the subject.

5. The method of claim 1, wherein the coronary atherosclerosis-related conditions comprises an ischemic injury of a tissue or organ caused by coronary atherosclerosis.

6. The method of claim 1, wherein the plasminogen has at least 75% sequence identity with SEQ ID No. 2, and still has the plasminogen activity.

7. The method of claim 1, wherein the plasminogen is a protein that comprises a plasminogen active fragment and still has the plasminogen activity.

8. The method of claim 1, wherein the plasminogen is selected from Glu-plasminogen, Lys-plasminogen, mini-plasminogen, micro-plasminogen, delta-plasminogen or their variants that retain the plasminogen activity.

9. The method of claim 1, wherein the plasminogen is a natural or synthetic human plasminogen, or a variant or fragment thereof that still retains the plasminogen activity.

10. The method of claim 1, wherein the plasminogen is administered to the subject at a dosage of 1-100 mg/kg at a frequency of weekly to daily.

11. The method of claim 10, wherein the dosage of the plasminogen is repeated at least once.

12. The method of claim 10, wherein the plasminogen is administered at least daily.

13. A method for preventing and/or treating atherosclerosis and its related conditions in a subject, comprising administering an effective amount of plasminogen to the subject, and wherein plasminogen promotes serum level of the high-density lipoprotein cholesterol (HDL-C) in the subject.

14. The method of claim 13, wherein the atherosclerosis comprises aortic atherosclerosis, coronary atherosclerosis, cerebral atherosclerosis, renal atherosclerosis, mesenteric atherosclerosis, and lower limb atherosclerosis.

15. The method of claim 13, wherein the atherosclerosis-related conditions comprise related conditions caused by tissue and organ ischemia due to atherosclerosis, comprising coronary heart disease, angina pectoris, myocardial infarction, arrhythmia, and heart failure caused by coronary atherosclerosis; cerebral ischemia, cerebral thrombosis, brain atrophy, cerebral hemorrhage, and cerebral embolism caused by cerebral atherosclerosis; renal insufficiency, hypertension, glomerular fibrosis, renal failure, and uremia caused by renal atherosclerosis; postprandial abdominal pain, dyspepsia, constipation, intestinal wall necrosis, and hemafecia caused by mesenteric atherosclerosis; and intermittent claudication,and gangrene caused by lower limb atherosclerosis.

16. The method of claim 13, wherein the atherosclerosis is atherosclerosis complicated with diabetes mellitus.

17. The method of claim 13, wherein the plasminogen prevents and/or treats atherosclerosis in one or more ways selected from: lowering a serum total cholesterol level in the subject, lowering a serum triglyceride level in the subject, lowering a serum low-density lipoprotein level in the subject, elevating a serum high-density lipoprotein level in the subject, reducing lipid deposition on an arterial wallof the subject, promoting fat metabolism in the liver, promoting fat transport in the liver, and reducing fat deposition in the liver of the subject.

18. The method of claim 13, wherein the atherosclerosis-related conditions comprise arterial thrombosis and its related conditions caused by atherosclerosis in the subject.

19. The method of claim 18, wherein the conditions comprise coronary heart disease, angina pectoris, myocardial infarction, arrhythmia, heart failure, cerebral ischemia, cerebral thrombosis, brain atrophy, cerebral hemorrhage, cerebral embolism, cerebral infarction, renal insufficiency, hypertension, glomerular fibrosis, renal failure, uremia, intestinal necrosis, intermittent claudication, and gangrene.

* * * * *

SEQUENCE LISTING

<160> NUMBER OF SEQ ID NOS: 14

<210> SEQ ID NO 1
<211> LENGTH: 2376

```
<212> TYPE: DNA
<213> ORGANISM: Artificial sequence
<220> FEATURE:
<223> OTHER INFORMATION: nucleotide sequence coding for the natural
      plasminogen (Glu-PLG,Glu-plasminogen)without the signal peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggaatgtat gcattgcagt ggagaaaact atgacggcaa atttccaag      540 accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact ttgtgacatc     720
ccccgctgca caacacctcc accatcttct ggtcccacct accagtgtct gaagggaaca     780 ggtgaaaaact atcgcgggaa tgtggctgtt accgtgtccg gcacacctg tcagcactgg     840 agtgcacaga cccctcacac acataacagg acaccagaaa acttcccctg caaaaatttg     900 gatgaaaaact actgccgcaa tcctgacgga aaagggccc atggtgcca tacaaccaac     960 agccaagtgc ggtgggagta ctgtaagata ccgtcctgtg actcctcccc agtatccacg    1020
gaacaattgg ctcccacagc accacctgag ctaaccctg tggtccagga ctgctaccat    1080
ggtgatggac agagctaccg aggcacatcc tccaccacca ccacaggaaa gaagtgtcag    1140
tcttggtcat ctatgacacc acaccggcac cagaagaccc cagaaaacta cccaaatgct    1200
ggcctgacaa tgaactactg caggaatcca gatgccgata aggcccctg tgtttttacc    1260 acagacccca gcgtcaggtg ggagtactgc aacctgaaaa aatgctcagg aacagaagcg    1320
agtgttgtag cacctccgcc tgttgtcctg cttccagatg tagagactcc ttccgaagaa    1380
gactgtatgt ttgggaatgg gaaaggatac cgaggcaaga gggcgaccac tgttactggg    1440
acgccatgcc aggactgggc tgcccaggag cccatagac acagcatttt cactccagag    1500
acaaatccac gggcgggtct ggaaaaaaat tactgccgta accctgatgg tgatgtaggt    1560 ggtcctggt gctacacgac aaatccaaga aaactttacg actactgtga tgtccctcag    1620
tgtgcggccc cttcatttga ttgtgggaag cctcaagtgg agccgaagaa atgtcctgga    1680
agggttgtag ggggtgtgt ggcccaccca cattcctggc cctggcaagt cagtcttaga    1740
acaaggtttg gaatgcactt ctgtggaggc accttgatat cccagagtg ggtgttgact    1800 gctgcccact gcttggagaa gtccccaagg ccttcatcct acaaggtcat cctgggtgca    1860
caccaagaag tgaatctcga accgcatgtt caggaaatag aagtgtctag gctgttcttg    1920
gagcccacac gaaaagatat tgccttgcta agctaagca gtcctgccgt catcactgac    1980
aaagtaatcc cagcttgtct gccatcccca aattatgtgg tcgctgaccg gaccgaatgt    2040
ttcatcactg gctggggaga aacccaaggt acttttggag ctggccttct caaggaagcc    2100
cagctccctg tgattgagaa taaagtgtgc aatcgctatg agtttctgaa tggaagagtc    2160
```

-continued

```
caatccaccg aactctgtgc tgggcatttg gccggaggca ctgacagttg ccagggtgac   2220
agtggaggtc ctctggtttg cttcgagaag gacaaataca ttttacaagg agtcacttct   2280
tggggtcttg gctgtgcacg ccccaataag cctggtgtct atgttcgtgt ttcaaggttt   2340
gttacttgga ttgagggagt gatgagaaat aattaa                              2376

<210> SEQ ID NO 2
<211> LENGTH: 791
<212> TYPE: PRT
<213> ORGANISM: Artificial sequence
<220> FEATURE:
<223> OTHER INFORMATION: amino acid sequence of the natural plasminogen
      (Glu-PLG,Glu-plasminogen) without the signal peptide

<400> SEQUENCE: 2

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320
```

```
Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
        340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
        435                 440                 445

Val Leu Leu Pro Asp Val Glu Thr Pro Ser Glu Glu Asp Cys Met Phe
        450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735
```

```
Cys Gln Gly Asp Ser Gly Gly Pro Leu Val Cys Phe Glu Lys Asp Lys
                 740                 745                 750
Tyr Ile Leu Gln Gly Val Thr Ser Trp Gly Leu Gly Cys Ala Arg Pro
             755                 760                 765
Asn Lys Pro Gly Val Tyr Val Arg Val Ser Arg Phe Val Thr Trp Ile
         770                 775                 780
Glu Gly Val Met Arg Asn Asn
785                 790
```

<210> SEQ ID NO 3
<211> LENGTH: 2433
<212> TYPE: DNA
<213> ORGANISM: Artificial sequence
<220> FEATURE:
<223> OTHER INFORMATION: nucleotide sequence coding for the natural plasminogen (from swiss prot)with the signal peptide

<400> SEQUENCE: 3

| | | | | | |
|---|---|---|---|---|---|
| atggaacata | aggaagtggt | tcttctactt | cttttatttc | tgaaatcagg | tcaaggagag | 60 |
| cctctggatg | actatgtgaa | tacccagggg | gcttcactgt | tcagtgtcac | taagaagcag | 120 |
| ctgggagcag | gaagtataga | agaatgtgca | gcaaaatgtg | aggaggacga | agaattcacc | 180 |
| tgcagggcat | tccaatatca | cagtaaagag | caacaatgtg | tgataatggc | tgaaaacagg | 240 |
| aagtcctcca | taatcattag | gatgagagat | gtagttttat | ttgaaaagaa | agtgtatctc | 300 |
| tcagagtgca | agactgggaa | tggaaagaac | tacagaggga | cgatgtccaa | aacaaaaaat | 360 |
| ggcatcacct | gtcaaaaatg | gagttccact | tctcccccaca | gacctagatt | ctcacctgct | 420 |
| acacacccct | cagagggact | ggaggagaac | tactgcagga | atccagacaa | cgatccgcag | 480 |
| gggcccctggt | gctatactac | tgatccagaa | aagagatatg | actactgcga | cattcttgag | 540 |
| tgtgaagagg | aatgtatgca | ttgcagtgga | gaaaactatg | acggcaaaat | ttccaagacc | 600 |
| atgtctggac | tggaatgcca | ggcctggac | tctcagagcc | cacacgctca | tggatacatt | 660 |
| ccttccaaat | ttccaaacaa | gaacctgaag | aagaattact | gtcgtaaccc | cgataggag | 720 |
| ctgcggcctt | ggtgtttcac | caccgacccc | aacaagcgct | gggaactttg | tgacatcccc | 780 |
| cgctgcacaa | cacctccacc | atcttctggt | cccacctacc | agtgtctgaa | gggaacaggt | 840 |
| gaaaactatc | gcgggaatgt | ggctgttacc | gtgtccgggc | acacctgtca | gcactggagt | 900 |
| gcacagaccc | ctcacacaca | taacaggaca | ccagaaaact | tccctgcaa | aaatttggat | 960 |
| gaaaactact | gccgcaatcc | tgacggaaaa | agggccccat | ggtgccatac | aaccaacagc | 1020 |
| caagtgcggt | gggagtactg | taagataccg | tcctgtgact | cctccccagt | atccacggaa | 1080 |
| caattggctc | ccacagcacc | acctgagcta | acccctgtgg | tccaggactg | ctaccatggt | 1140 |
| gatggacaga | gctaccgagg | cacatcctcc | accaccacca | caggaaagaa | gtgtcagtct | 1200 |
| tggtcatcta | tgacaccaca | ccggcaccag | aagacccag | aaaactaccc | aaatgctggc | 1260 |
| ctgacaatga | actactgcag | gaatccagat | gccgataaag | gccccctggtg | ttttaccaca | 1320 |
| gaccccagcg | tcaggtggga | gtactgcaac | ctgaaaaaat | gctcaggaac | agaagcgagt | 1380 |
| gttgtagcac | ctccgcctgt | tgtcctgctt | ccagatgtag | agactccttc | cgaagaagac | 1440 |
| tgtatgtttg | ggaatgggaa | aggatacccga | ggcaagaggg | cgaccactgt | tactgggacg | 1500 |
| ccatgccagg | actgggctgc | ccaggagccc | catagacaca | gcattttcac | tccagagaca | 1560 |
| aatccacggg | cgggtctgga | aaaaaattac | tgccgtaacc | ctgatggtga | tgtaggtggt | 1620 |
| ccctggtgct | acacgacaaa | tccaagaaaa | ctttacgact | actgtgatgt | ccctcagtgt | 1680 |

```
gcggcccctt catttgattg tgggaagcct caagtggagc cgaagaaatg tcctggaagg    1740
gttgtagggg ggtgtgtggc ccacccacat tcctggccct ggcaagtcag tcttagaaca    1800
aggtttggaa tgcacttctg tggaggcacc ttgatatccc cagagtgggt gttgactgct    1860
gcccactgct tggagaagtc cccaaggcct tcatcctaca aggtcatcct gggtgcacac    1920
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat taa                                 2433
```

<210> SEQ ID NO 4
<211> LENGTH: 810
<212> TYPE: PRT
<213> ORGANISM: Artificial sequence
<220> FEATURE:
<223> OTHER INFORMATION: amino acid sequence coding for the natural
      plasminogen (from swiss prot)with the signal peptide

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220
```

```
Pro Asn Lys Asn Leu Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
            245                 250                 255

Cys Asp Ile Pro Arg Cys Thr Thr Pro Pro Ser Ser Gly Pro Thr
        260                 265                 270

Tyr Gln Cys Leu Lys Gly Thr Gly Glu Asn Tyr Arg Gly Asn Val Ala
    275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
```

645                 650                 655
Leu Phe Leu Glu Pro Thr Arg Lys Asp Ile Ala Leu Leu Lys Leu Ser
             660                 665                 670

Ser Pro Ala Val Ile Thr Asp Lys Val Ile Pro Ala Cys Leu Pro Ser
             675                 680                 685

Pro Asn Tyr Val Val Ala Asp Arg Thr Glu Cys Phe Ile Thr Gly Trp
             690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                 725                 730                 735

Gly Arg Val Gln Ser Thr Glu Leu Cys Ala Gly His Leu Ala Gly Gly
             740                 745                 750

Thr Asp Ser Cys Gln Gly Asp Ser Gly Gly Pro Leu Val Cys Phe Glu
             755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                 805                 810

<210> SEQ ID NO 5
<211> LENGTH: 2145
<212> TYPE: DNA
<213> ORGANISM: Artificial sequence
<220> FEATURE:
<223> OTHER INFORMATION: nucleotide sequence coding for LYS77-PLG(Lys-
      plasminogen)

<400> SEQUENCE: 5
aaagtgtatc tctcagagtg caagactggg aatggaaaga actacagagg gacgatgtcc      60
aaaacaaaaa atggcatcac ctgtcaaaaa tggagttcca cttctcccca cagacctaga     120
ttctcacctg ctacacaccc ctcagaggga ctggaggaga actactgcag gaatccagac     180
aacgatccgc aggggccctg tgctatact actgatccag aaaagagata tgactactgc      240
gacattcttg agtgtgaaga ggaatgtatg cattgcagtg agaaaactat tgacggcaaa     300
atttccaaga ccatgtctgg actggaatgc caggcctggg actctcagag cccacacgct     360
catggataca ttccttccaa atttccaaac aagaacctga agaagaatta ctgtcgtaac     420
cccgataggg agctgcggcc ttggtgtttc accaccgacc caacaagcg ctgggaactt      480 tgtgacatcc cccgctgcac aacacctcca ccatcttctg gtcccaccta ccagtgtctg     540
aagggaacag gtgaaaacta tcgcgggaat gtggctgtta ccgtgtccgg gcacacctgt     600
cagcactgga gtgcacagac ccctcacaca cataacagga caccagaaaa cttcccctgc     660
aaaaatttgg atgaaaacta ctgccgcaat cctgacggaa aaagggcccc atggtgccat     720
acaaccaaca gccaagtgcg gtgggagtac tgtaagatac cgtcctgtga ctcctcccca     780
gtatccacgg aacaattggc tcccacagca ccacctgagc taaccccctgt ggtccaggac     840 tgctaccatg gtgatggaca gagctaccga ggcacatcct ccaccaccac acaggaaag     900 aagtgtcagt cttggtcatc tatgacacca caccggcacc agaagacccc agaaaactac     960
ccaaatgctg gcctgacaat gaactactgc aggaatccag atgccgataa aggcccctgg    1020
tgttttacca cagaccccag cgtcaggtgg gagtactgca acctgaaaaa atgctcagga    1080

| | | |
|---|---|---|
| acagaagcga gtgttgtagc acctccgcct gttgtcctgc ttccagatgt agagactcct | | 1140 |
| tccgaagaag actgtatgtt tgggaatggg aaaggatacc gaggcaagag ggcgaccact | | 1200 |
| gttactggga cgccatgcca ggactgggct gcccaggagc cccatagaca cagcattttc | | 1260 |
| actccagaga caaatccacg ggcgggtctg gaaaaaaatt actgccgtaa ccctgatggt | | 1320 |
| gatgtaggtg gtccctggtg ctacacgaca aatccaagaa aactttacga ctactgtgat | | 1380 |
| gtccctcagt gtgcggcccc ttcatttgat tgtgggaagc ctcaagtgga gccgaagaaa | | 1440 |
| tgtcctggaa gggttgtagg ggggtgtgtg gcccacccac attcctggcc ctggcaagtc | | 1500 |
| agtcttagaa caaggtttgg aatgcacttc tgtggaggca ccttgatatc cccagagtgg | | 1560 |
| gtgttgactg ctgcccactg cttggagaag tccccaaggc cttcatccta caaggtcatc | | 1620 |
| ctgggtgcac accaagaagt gaatctcgaa ccgcatgttc aggaaataga agtgtctagg | | 1680 |
| ctgttcttgg agcccacacg aaaagatatt gccttgctaa agctaagcag tcctgccgtc | | 1740 |
| atcactgaca aagtaatccc agcttgtctg ccatccccaa attatgtggt cgctgaccgg | | 1800 |
| accgaatgtt tcatcactgg ctggggagaa acccaaggta cttttggagc tggccttctc | | 1860 |
| aaggaagccc agctccctgt gattgagaat aaagtgtgca atcgctatga gtttctgaat | | 1920 |
| ggaagagtcc aatccaccga actctgtgct gggcatttgg ccggaggcac tgacagttgc | | 1980 |
| cagggtgaca gtggaggtcc tctggtttgc ttcgagaagg acaaatacat tttacaagga | | 2040 |
| gtcacttctt ggggtcttgg ctgtgcacgc cccaataagc ctggtgtcta tgttcgtgtt | | 2100 |
| tcaaggtttg ttacttggat tgagggagtg atgagaaata attaa | | 2145 |

<210> SEQ ID NO 6
<211> LENGTH: 714
<212> TYPE: PRT
<213> ORGANISM: Artificial sequence
<220> FEATURE:
<223> OTHER INFORMATION: amino acid sequence of LYS77-PLG(Lys-plasminogen)

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175
```

-continued

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

```
Pro Asn Tyr Val Val Ala Asp Arg Thr Glu Cys Phe Ile Thr Gly Trp
            595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial sequence
<220> FEATURE:
<223> OTHER INFORMATION: nucleotide sequence coding for delta-plg(delta-
      plasminogen)

<400> SEQUENCE: 7
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc aaaacaaaa      300 aatggcatca cctgtcaaaa atggagttcc acttctcccc acagacctag attctcacct     360
gctacacacc cctcagaggg actggaggag aactactgca ggaatccaga caacgatccg     420 caggggcct  ggtgctatac tactgatcca gaaaagagat atgactactg cgacattctt     480
gagtgtgaag aggcggcccc ttcatttgat tgtgggaagc ctcaagtgga gccgaagaaa     540
tgtcctggaa gggttgtagg ggggtgtgtg gcccacccac attcctggcc ctggcaagtc     600
agtcttagaa caaggtttgg aatgcacttc tgtggaggca ccttgatatc cccagagtgg     660
gtgttgactg ctgcccactg cttggagaag tccccaaggc cttcatccta caaggtcatc     720
ctgggtgcac accaagaagt gaatctcgaa ccgcatgttc aggaaataga agtgtctagg     780
ctgttcttgg agcccacacg aaaagatatt gccttgctaa agctaagcag tcctgccgtc     840
atcactgaca aagtaatccc agcttgtctg ccatccccaa attatgtggt cgctgaccgg     900
accgaatgtt tcatcactgg ctggggagaa acccaaggta cttttggagc tggccttctc     960
aaggaagccc agctccctgt gattgagaat aaagtgtgca atcgctatga gtttctgaat    1020
ggaagagtcc aatccaccga actctgtgct gggcatttgg ccggaggcac tgacagttgc    1080
cagggtgaca gtggaggtcc tctggtttgc ttcgagaagg acaaatacat tttacaagga    1140
gtcacttctt ggggtcttgg ctgtgcacgc cccaataagc ctggtgtcta tgttcgtgtt    1200
tcaaggtttg ttacttggat tgagggagtg atgagaaata attaa                   1245

<210> SEQ ID NO 8
```

<211> LENGTH: 414
<212> TYPE: PRT
<213> ORGANISM: Artificial sequence
<220> FEATURE:
<223> OTHER INFORMATION: amino acid sequence of delta-plg(delta-plasminogen)

<400> SEQUENCE: 8

| | | | | | | | | | | | | | | | |
|---|---|---|---|---|---|---|---|---|---|---|---|---|---|---|---|
| Glu | Pro | Leu | Asp | Asp | Tyr | Val | Asn | Thr | Gln | Gly | Ala | Ser | Leu | Phe | Ser |
| 1 | | | | 5 | | | | | 10 | | | | | 15 | |
| Val | Thr | Lys | Lys | Gln | Leu | Gly | Ala | Gly | Ser | Ile | Glu | Glu | Cys | Ala | Ala |
| | | | 20 | | | | | 25 | | | | | 30 | | |
| Lys | Cys | Glu | Glu | Asp | Glu | Glu | Phe | Thr | Cys | Arg | Ala | Phe | Gln | Tyr | His |
| | | | 35 | | | | | 40 | | | | | 45 | | |
| Ser | Lys | Glu | Gln | Gln | Cys | Val | Ile | Met | Ala | Glu | Asn | Arg | Lys | Ser | Ser |
| | 50 | | | | | 55 | | | | | 60 | | | | |
| Ile | Ile | Ile | Arg | Met | Arg | Asp | Val | Val | Leu | Phe | Glu | Lys | Lys | Val | Tyr |
| 65 | | | | | 70 | | | | | 75 | | | | | 80 |
| Leu | Ser | Glu | Cys | Lys | Thr | Gly | Asn | Gly | Lys | Asn | Tyr | Arg | Gly | Thr | Met |
| | | | | 85 | | | | | 90 | | | | | 95 | |
| Ser | Lys | Thr | Lys | Asn | Gly | Ile | Thr | Cys | Gln | Lys | Trp | Ser | Ser | Thr | Ser |
| | | | 100 | | | | | 105 | | | | | 110 | | |
| Pro | His | Arg | Pro | Arg | Phe | Ser | Pro | Ala | Thr | His | Pro | Ser | Glu | Gly | Leu |
| | | | 115 | | | | | 120 | | | | | 125 | | |
| Glu | Glu | Asn | Tyr | Cys | Arg | Asn | Pro | Asp | Asn | Asp | Pro | Gln | Gly | Pro | Trp |
| | 130 | | | | | 135 | | | | | 140 | | | | |
| Cys | Tyr | Thr | Thr | Asp | Pro | Glu | Lys | Arg | Tyr | Asp | Tyr | Cys | Asp | Ile | Leu |
| 145 | | | | | 150 | | | | | 155 | | | | | 160 |
| Glu | Cys | Glu | Glu | Ala | Ala | Pro | Ser | Phe | Asp | Cys | Gly | Lys | Pro | Gln | Val |
| | | | | 165 | | | | | 170 | | | | | 175 | |
| Glu | Pro | Lys | Lys | Cys | Pro | Gly | Arg | Val | Val | Gly | Gly | Cys | Val | Ala | His |
| | | | 180 | | | | | 185 | | | | | 190 | | |
| Pro | His | Ser | Trp | Pro | Trp | Gln | Val | Ser | Leu | Arg | Thr | Arg | Phe | Gly | Met |
| | | | 195 | | | | | 200 | | | | | 205 | | |
| His | Phe | Cys | Gly | Gly | Thr | Leu | Ile | Ser | Pro | Glu | Trp | Val | Leu | Thr | Ala |
| | 210 | | | | | 215 | | | | | 220 | | | | |
| Ala | His | Cys | Leu | Glu | Lys | Ser | Pro | Arg | Pro | Ser | Ser | Tyr | Lys | Val | Ile |
| 225 | | | | | 230 | | | | | 235 | | | | | 240 |
| Leu | Gly | Ala | His | Gln | Glu | Val | Asn | Leu | Glu | Pro | His | Val | Gln | Glu | Ile |
| | | | | 245 | | | | | 250 | | | | | 255 | |
| Glu | Val | Ser | Arg | Leu | Phe | Leu | Glu | Pro | Thr | Arg | Lys | Asp | Ile | Ala | Leu |
| | | | 260 | | | | | 265 | | | | | 270 | | |
| Leu | Lys | Leu | Ser | Ser | Pro | Ala | Val | Ile | Thr | Asp | Lys | Val | Ile | Pro | Ala |
| | | | 275 | | | | | 280 | | | | | 285 | | |
| Cys | Leu | Pro | Ser | Pro | Asn | Tyr | Val | Val | Ala | Asp | Arg | Thr | Glu | Cys | Phe |
| | 290 | | | | | 295 | | | | | 300 | | | | |
| Ile | Thr | Gly | Trp | Gly | Glu | Thr | Gln | Gly | Thr | Phe | Gly | Ala | Gly | Leu | Leu |
| 305 | | | | | 310 | | | | | 315 | | | | | 320 |
| Lys | Glu | Ala | Gln | Leu | Pro | Val | Ile | Glu | Asn | Lys | Val | Cys | Asn | Arg | Tyr |
| | | | | 325 | | | | | 330 | | | | | 335 | |
| Glu | Phe | Leu | Asn | Gly | Arg | Val | Gln | Ser | Thr | Glu | Leu | Cys | Ala | Gly | His |
| | | | 340 | | | | | 345 | | | | | 350 | | |
| Leu | Ala | Gly | Gly | Thr | Asp | Ser | Cys | Gln | Gly | Asp | Ser | Gly | Gly | Pro | Leu |
| | | | 355 | | | | | 360 | | | | | 365 | | |
| Val | Cys | Phe | Glu | Lys | Asp | Lys | Tyr | Ile | Leu | Gln | Gly | Val | Thr | Ser | Trp |

```
                    370                375                380
Gly Leu Gly Cys Ala Arg Pro Asn Lys Pro Gly Val Tyr Val Arg Val
385                 390                395                 400

Ser Arg Phe Val Thr Trp Ile Glu Gly Val Met Arg Asn Asn
                    405                410
```

<210> SEQ ID NO 9
<211> LENGTH: 1104
<212> TYPE: DNA
<213> ORGANISM: Artificial sequence
<220> FEATURE:
<223> OTHER INFORMATION: nucleotide sequence coding for Mini-plg(mini-
      plasminogen)

<400> SEQUENCE: 9

```
gtcaggtggg agtactgcaa cctgaaaaaa tgctcaggaa cagaagcgag tgttgtagca    60
cctccgcctg ttgtcctgct tccagatgta gagactcctt ccgaagaaga ctgtatgttt   120
gggaatggga aaggataccg aggcaagagg gcgaccactg ttactgggac gccatgccag   180
gactgggctg cccaggagcc catagacaca gcattttca ctccagagac aaatccacgg    240
gcgggtctgg aaaaaaatta ctgccgtaac cctgatggtg atgtaggtgg tccctggtgc   300
tacacgacaa atccaagaaa actttacgac tactgtgatg tccctcagtg tgcggcccct   360
tcatttgatt gtgggaagcc tcaagtggag ccgaagaaat gtcctggaag ggttgtaggg   420
gggtgtgtgg cccacccaca ttcctggccc tggcaagtca gtcttagaac aaggtttgga   480
atgcacttct gtggaggcac cttgatatcc ccagagtggg tgttgactgc tgcccactgc   540
ttggagaagt ccccaaggcc ttcatcctac aaggtcatcc tgggtgcaca ccaagaagtg   600
aatctcgaac cgcatgttca ggaaatagaa gtgtctaggc tgttcttgga gcccacacga   660
aaagatattg ccttgctaaa gctaagcagt cctgccgtca tcactgacaa agtaatccca   720
gcttgtctgc catccccaaa ttatgtggtc gctgaccgga ccgaatgttt catcactggc   780
tggggagaaa cccaaggtac ttttggagct ggccttctca aggaagccca gctccctgtg   840
attgagaata agtgtgcaa tcgctatgag tttctgaatg gaagagtcca atccaccgaa   900
ctctgtgctg gcatttggc cggaggcact gacagttgcc agggtgacag tggaggtcct   960
ctggtttgct tcgagaagga caaatacatt ttacaaggag tcacttcttg gggtcttggc  1020
tgtgcacgcc ccaataagcc tggtgtctat gttcgtgttt caaggtttgt tacttggatt  1080
gagggagtga tgagaaataa ttaa                                         1104
```

<210> SEQ ID NO 10
<211> LENGTH: 367
<212> TYPE: PRT
<213> ORGANISM: Artificial sequence
<220> FEATURE:
<223> OTHER INFORMATION: amino acid sequence of Mini-plg(mini-
      plasminogen)

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60
```

```
Gln Glu Pro His Arg His Ser Ile Phe Thr Pro Glu Thr Asn Pro Arg
 65                  70                  75                  80

Ala Gly Leu Glu Lys Asn Tyr Cys Arg Asn Pro Asp Gly Asp Val Gly
                 85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205

Ile Glu Val Ser Arg Leu Phe Leu Glu Pro Thr Arg Lys Asp Ile Ala
210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
    290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
        355                 360                 365

<210> SEQ ID NO 11
<211> LENGTH: 750
<212> TYPE: DNA
<213> ORGANISM: Artificial sequence
<220> FEATURE:
<223> OTHER INFORMATION: nucleotide sequence coding for Micro-plg(micro-
      plasminogen)

<400> SEQUENCE: 11
gccccttcat tgattgtgg gaagcctcaa gtggagccga agaaatgtcc tggaagggtt      60 gtagggggt gtgtggccca cccacattcc tggccctggc aagtcagtct tagaacaagg    120 tttgaatgc acttctgtgg aggcaccttg atatcccag agtgggtgtt gactgctgcc     180
cactgcttgg agaagtcccc aaggccttca tcctacaagg tcatcctggg tgcacaccaa   240
gaagtgaatc tcgaaccgca tgttcaggaa atagaagtgt ctaggctgtt cttggagccc   300
```

```
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750
```

```
<210> SEQ ID NO 12
<211> LENGTH: 249
<212> TYPE: PRT
<213> ORGANISM: Artificial sequence
<220> FEATURE:
<223> OTHER INFORMATION: amino acid sequence coding for Micro-plg(micro-
      plasminogen)

<400> SEQUENCE: 12
```

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

```
<210> SEQ ID NO 13
<211> LENGTH: 684
<212> TYPE: DNA
```

<213> ORGANISM: Artificial sequence
<220> FEATURE:
<223> OTHER INFORMATION: nucleotide sequence coding for the serine
     protease domain

<400> SEQUENCE: 13

```
gttgtagggg ggtgtgtggc ccacccacat tcctggccct ggcaagtcag tcttagaaca      60
aggtttggaa tgcacttctg tggaggcacc ttgatatccc cagagtgggt gttgactgct     120
gcccactgct tggagaagtc cccaaggcct tcatcctaca aggtcatcct gggtgcacac     180
caagaagtga atctcgaacc gcatgttcag gaaatagaag tgtctaggct gttcttggag     240
cccacacgaa aagatattgc cttgctaaag ctaagcagtc ctgccgtcat cactgacaaa     300
gtaatcccag cttgtctgcc atccccaaat tatgtggtcg ctgaccggac cgaatgtttc     360
atcactggct ggggagaaac ccaaggtact tttggagctg gccttctcaa ggaagcccag     420
ctccctgtga ttgagaataa agtgtgcaat cgctatgagt ttctgaatgg aagagtccaa     480
tccaccgaac tctgtgctgg gcatttggcc ggaggcactg acagttgcca gggtgacagt     540
ggaggtcctc tggtttgctt cgagaaggac aaatacattt tacaaggagt cacttcttgg     600
ggtcttggct gtgcacgccc caataagcct ggtgtctatg ttcgtgtttc aaggtttgtt     660
acttggattg agggagtgat gaga                                            684
```

<210> SEQ ID NO 14
<211> LENGTH: 228
<212> TYPE: PRT
<213> ORGANISM: Artificial sequence
<220> FEATURE:
<223> OTHER INFORMATION: amino acid sequence coding for the serine
     protease domain

<400> SEQUENCE: 14

```
Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
```

```
                195                 200                 205
Lys Pro Gly Val Tyr Val Arg Val Ser Arg Phe Val Thr Trp Ile Glu
    210                 215                 220

Gly Val Met Arg
225
```